(12) United States Patent
Slattum et al.

(10) Patent No.: US 7,326,780 B2
(45) Date of Patent: *Feb. 5, 2008

(54) COMPOUNDS AND PROCESSES FOR SINGLE-POT ATTACHMENT OF A LABEL TO NUCLEIC ACID

(75) Inventors: Paul M. Slattum, Madison, WI (US); Jon A. Wolff, Madison, WI (US); James E. Hagstrom, Middleton, WI (US); Vladimir G. Budker, Middleton, WI (US)

(73) Assignee: Mirus Bio Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/415,021

(22) Filed: May 1, 2006

(65) Prior Publication Data
US 2006/0188927 A1    Aug. 24, 2006

Related U.S. Application Data

(60) Division of application No. 10/356,222, filed on Jan. 31, 2003, now abandoned, which is a continuation-in-part of application No. 10/413,942, filed on Apr. 15, 2003, which is a division of application No. 09/767,794, filed on Jan. 23, 2001, now Pat. No. 6,593,465, which is a division of application No. 08/982,485, filed on Dec. 2, 1997, now Pat. No. 6,262,252.

(60) Provisional application No. 60/046,952, filed on May 19, 1997.

(51) Int. Cl.
*C07H 21/00* (2006.01)
*C07H 21/02* (2006.01)
*C07H 21/04* (2006.01)
*C12Q 1/68* (2006.01)
*G01N 33/53* (2006.01)

(52) U.S. Cl. ...................................... 536/23.1
(58) Field of Classification Search ............... 536/23.1, 536/26.6; 436/800, 6
See application file for complete search history.

(56) References Cited

FOREIGN PATENT DOCUMENTS

GB            769440      *  3/1957
WO        WO 98/52961    * 11/1998

OTHER PUBLICATIONS

Mattes et al. Nucleic Acids Research, 1986, vol. 14, No. 7, pp. 2971-2987.*

* cited by examiner

*Primary Examiner*—Jezia Riley
(74) *Attorney, Agent, or Firm*—Kirk Ekena; Mark K. Johnson

(57) ABSTRACT

Compounds and methods are provided for a single-pot covalent attachment of a label to nucleic acids comprising forming a covalently attachable labeling reagent for alkylating the molecule. Then, combining the covalently attachable labeling reagent with a mixture containing the molecule, under conditions wherein the labeling reagent has reactivity with the molecule thereby forming a covalent bond.

17 Claims, 23 Drawing Sheets

*i.* LABEL-IT®-Thiazole orange

*ii.* LABEL-IT®-Cyanine5

*iii.* LABEL-IT®-Cyanine3

A.

D–B–A

B.

A.

B.

C.

D.

E.

i. LABEL-IT®-Thiazole orange ii. LABEL-IT®-Cyanine5 iii. LABEL-IT®-Cyanine3 i. LABEL-IT®-Carboxylic acid ii. LABEL-IT®-Amine iii. LABEL-IT®-Diamine iv. LABEL-IT®-Triamine

*v.* LABEL-IT®-Tetra-amine

*vi.* LABEL-IT®-Hexamine

*vii.* LABEL-IT®-Bromoacetamide

*viii.* LABEL-IT®-Dibromoacetamide

*ix.* LABEL-IT®-PDP

*x.* LABEL-IT®-Cysteine-PDP

*i*. Di-LABEL-IT®

*ii*. Tri-LABEL-IT®

*i.* LABEL-IT®-Polyacid chelator

*ii.* LABEL-IT®-Chelator

*i.* LABEL-IT®-DNP

*ii.* LABEL-IT®-Hexaethyleneglycol-Biotin

*iii.* LABEL-IT®-PEG$_{3400}$-Biotin

*i.* LABEL-IT®-TAT

*ii.* LABEL-IT®-PolyHistidine

*iii.* LABEL-IT®-NLS

*i.* LABEL-IT®-Diamine-Rhodamine

*ii.* LABEL-IT®-Rhodamine Hexaethyleneglycol-Biotin

*i.* LABEL-IT®-Dioleoyl

*ii.* LABEL-IT®-Stearyl

A.

B.

C.

D.

E.

F.

A. LABEL-IT®-amine II

B. neutral LABEL-IT®-Cyanine3

C. neutral LABEL-IT®-Cyanine5

D. neutral LABEL-IT®-PEG-Cyanine5

E. neutral LABEL-IT®-ALEXA™488

A.

B.

C.

D.

E.

F.

A.

B.

A.

B.

C.

A. charge reversible LABEL-IT®

B. charge reversible LABEL-IT®-Cyanine3

C. charge reversible LABEL-IT®-CX-Rhodamine

D. charge reversed LABEL-IT®-CX-rhodamine

COMPOUNDS AND PROCESSES FOR SINGLE-POT ATTACHMENT OF A LABEL TO NUCLEIC ACID

CROSS-REFERENCE TO RELATED APPLICATIONS

This application is divisional of application Ser. No. 10/356,222 now abandoned, filed Jan. 31, 2003, and a continuation-in-part of application Ser. No. 10/413,942, filed Apr. 15, 2003, which is a divisional of application Ser. No. 09/767,794, filed Jan. 23, 2001, issued as U.S. Pat. No. 6,593,465, which is a divisional of application Ser. No. 08/982,485, filed Dec. 2, 1997, issued as U.S. Pat. No. 6,262,252, which claims the benefit of U.S. Provisional Application No. 60/046,952, filed May 19, 1997.

FIELD OF THE INVENTION

The described invention relates to compounds and methods for covalently attaching a label to a nucleic acid. More specifically, the compounds are alkylating compounds having a label molecule and the covalent attachment is performed by a one-pot alkylation reaction.

BACKGROUND OF THE INVENTION

The analysis and detection of minute quantities of substances in biological and non-biological samples has become a routine practice in clinical and analytical laboratories. These detection techniques can be divided into two major classes: (1) those based on ligand-receptor interactions (e.g., immunoassay-based techniques) and (2) those based on nucleic acid hybridization (polynucleotide sequence-based techniques).

Immunoassay-based techniques are characterized by a sequence of steps comprising the non-covalent binding of an antibody and an antigen complementary to it. Polynucleotide sequence-based detection techniques have been characterized by a sequence of steps comprising the non-covalent binding of a labeled polynucleotide sequence or probe to a complementary sequence of the analyte under conditions which permit hybridization of the bases through Watson-Crick pairing, and the detection of that hybridization.

The non-covalent binding of a labeled sequence or probe to a complementary sequence of a nucleic acid is the primary recognition event of polynucleotide sequence-based detection techniques. This binding event is brought about by a precise molecular alignment and interaction of complementary nucleotides of the probe and target. It is energetically favored by the release of non-covalent bonding free energy, e.g., hydrogen bonding, stacking free energy and the like.

In order to employ the non-covalent binding of a probe for the determination of a nucleic acid containing a target sequence, it is necessary to be able to detect binding of the probe to the target. This detection is effected through a signaling step or event. A signaling step or event allows detection in some quantitative or qualitative manner of the occurrence of the primary recognition event.

A wide variety of signaling events may be employed to detect the occurrence of the primary recognition event. The signaling event chosen depends on the particular signal that characterizes the reporter molecule employed. Although the labeling reagent itself—without further treatment—may be detectable, more often, either the reporter molecule is attached covalently, or bound non-covalently to a labeling reagent.

There are a wide variety of reporter molecules that may be employed for covalent attachment to the labeling reagent of polynucleotide sequences useful as probes in nucleic acid detection systems. All that is required is that the reporter molecule provide a signal that may be detected by appropriate means and that has the ability to attach covalently to the labeling reagent.

Reporter molecules may be radioactive or non-radioactive. Radioactive signaling moieties are characterized by one or more radioisotopes of phosphorous, iodine, hydrogen, carbon, cobalt, nickel, and the like. Preferably the radioisotope emits $\beta$ or $\gamma$ radiation, and has a long half-life. Detection of radioactive reporter molecules is typically accomplished by the stimulation of photon emission from crystalline detectors caused by the radiation, or by the fogging of a photographic emulsion.

Non-radioactive reporter molecules have the advantage that their use does not pose the hazards associated with exposure to radiation, and that special disposal techniques after use are not required. In addition, they are generally more stable, and as a consequence, cheaper to use. Detection sensitivities of non-radioactive reporter molecules may be as high or higher than those of radioactive reporter molecules.

The ability to label nucleic acid with a non-radioactive detectable marker simply and reliably makes it attractive for use in a wide variety of molecular and cellular biology applications. Some specific applications in which a non-radioactively labeled nucleic acid probe can be used include hybridization reaction procedures (southern, northern, slot, or dot blots, in situ hybridization), nucleic acid localization studies, DNA or RNA quantitation and DNase or RNase quantitation.

Both enzyme mediated and direct labeling protocols have been developed to attach non-radioactive detectable tags such as the fluorescent compounds fluorescein and rhodamine (and others) to DNA. While these labeling methods have allowed non-radioactive detection systems to approach or even surpass the radioactive methods in terms of sensitivity there remains significant disadvantages with each of the non-radioactive labeling systems developed to date. 1) Enzymatic DNA labeling systems require a number of reagents including both unlabeled and labeled nucleotide precursors, primers, and/or enzymes to facilitate DNA synthesis. Labeling efficiency is not easily controlled and for the two most common labeling reactions (nick translation and random priming) it is not possible to create a labeled probe that is the same size as the starting DNA. 2) Direct labeling methods also have significant limitations which include a lower efficiency of labeling resulting in reduced sensitivity, laborious multi-step labeling protocols, harsh reaction conditions, variability from reaction to reaction, and unstable reactants.

Direct labeling methods have been developed for chemically modifying nucleic acids for use as detectable probes in hybridization experiments. Sodium bisulfite may be used in the presence of a diamine to introduce primary amines on cytosine residues which could then be subsequently modified with a reporter group. Adarichev et al. 1995 used 4-aminohydroxybutylamine to transaminate cytosine residues in a similar fashion. DNA has been modified at the C-8 position of adenine or guanine using a diazonium salt attached to biotin. The diazonium salt is generated in situ with sodium nitrite then directly reacted with DNA. In another labeling procedure, the carcinogen 2-acetylaminofluorene was modified to the reactive compound N-acetoxy-2-acetylaminofluorene by Landegent et al and attached to the C-8 position of guanine. DNA modified by this reagent was subsequently detected using antibodies directed against the modified guanosine. The reactive aldehyde at the C8 position ($N^7$-formyl group) of a ring-opened guanine has also been used as a target for direct labeling using an aldehyde reactive nucleophile such as hydrazine attached to a detectable label.

These reagents have different limitations; some of these limitations are multi-step synthesis, the ability to derivatize only single stranded DNA, the need to use large amounts of reagent or other harsh conditions to get adequate amounts of DNA modification, and the modification of amines involved in double-stranded DNA base pairing.

The techniques of Northern and Southern blotting are two of the most powerful and frequently used procedures in molecular biology. Yet the necessary manipulations are time consuming and are not likely to be automated under current technology. Often the polynucleotide (RNA, DNA) under analysis must first be fractionated by size, transferred onto a solid support and then treated through a series of steps to ensure only specific binding of a probe. Detection of the hybridized products usually depends on radiolabeling, heavy metal derivatization or antibody complexation. The methods of blotting have been a staple of basic research, and now also serve in an ever increasing number of commercial kits used to diagnose genetic, malignant, and infectious diseases.

In 1967 Belikova et al. first described monoadduct alkylation of ribonucleosides and diribonucleoside phosphates using 2-chloroethylamine residues. While this work provided evidence that ribonucleosides could be covalently modified with the alkylating mustard derivative, the efficiency of the process was very low. Utilizing a multi-step process Frumgarts et al. 1986 alkylated DNA using the nitrogen mustard 4-(N-methylamino-N-2-chloroethyl)benzylamine, and subsequently attached fluorescent labels to the amine that had been covalently attached to the DNA. This multi-step process required that the mustard and fluorescent label be used in a large molar excess to the DNA being labeled.

Quinacrine (acridine) is a DNA intercalating molecule which is also fluorescent. Caspersson et al. 1969 used this molecule both with and without the attachment of a nitrogen mustard to obtain chemical and physicochemical information about metaphase chromosomal structure. In this study, the fluorescent pattern obtained using aquamarine, which contains no alkylating group, produced a band pattern of the same type as the quinacrine mustard.

SUMMARY OF THE INVENTION

In a preferred embodiment, we describe nucleic acid labeling reagents that utilize the nucleic acid alkylating ability of mustards and three-membered ring compounds. The components of the labeling reagent consist of a mustard or three-membered ring moiety and a label or tag. The labeling reagent may also contain a linker or spacer group and/or an affinity group. Mustards include nitrogen, sulfur and selenium mustards. Three-membered ring compounds include those with nitrogen, sulfur, and oxygen heteroatoms. A reactive nitrogen mustard derivative used in the synthesis of these labeling agents can be the aromatic nitrogen mustard 4-[(2-chloroethyl)-methylamino]-benzaldehyde. This nitrogen mustard derivative was described in U.S. Pat. No. 2,141,090. The described reagents can be used to covalently attach a label to an imine nitrogen, such as at the N7 position of guanine or at the N3 position of adenine. The label or tag can be a detectable marker or a functional group. The label can be used to detect the nucleic acid, to attach a functional group to the nucleic acid, or to covalently or non-covalently crosslink the labeled-nucleic acid to another compound.

In a preferred embodiment, we describe a nucleic acid labeling method that combines one-pot simplicity with high efficiency labeling and results in a labeled nucleic acid that remains intact and stable. The procedure for labeling results in the formation of a covalent bond between the labeling reagent and the nucleic acid. The labeling procedure comprises: forming a covalently attachable labeling reagent for alkylating the nucleic acid, combining the labeling reagent with a mixture containing the nucleic acid under conditions wherein the labeling reagent has reactivity with the nucleic acid thereby forming a covalent bond, and separation of the labeled nucleic acid from the unreacted labeling reagent. The extent of labeling can be controlled by regulating the relative amounts of labeling reagent and nucleic acid, by adjusting the length of the incubation of the labeling reagent with the nucleic acid, by controlling the temperature of the incubation, by controlling the absolute concentrations of the nucleic acid and labeling reagent, and by controlling the composition of the aqueous or organic solution in which the labeling reaction occurs.

In a preferred embodiment, we describe compounds, called labeling reagents, for the covalent attachment of a label to nucleic acid comprising: an alkylating group covalently linked to a label wherein the labeling reagent has affinity for nucleic acid when the bond between the labeling reagent and the nucleic acid is formed. The alkylating group may be a mustard or a three-membered ring containing group selected from the list comprising: nitrogen mustards, sulfur mustards, aziridines, oxiranes (epoxides), episulfides, and cyclopropanes. A preferred nitrogen mustard is an aromatic mustard. A preferred aromatic mustard is an aromatic tertiary nitrogen mustard. A preferred aromatic tertiary nitrogen mustard is 4-[(2-chloroethyl)-methylamino]-benzaldehyde. The label may be selected from the group comprising: fluorescence-emitting compounds, radioactive compounds, haptens, immunogenic molecules, chemiluminescence-emitting compounds, proteins, and functional groups. Preferred fluorescence-emitting compounds are fluorescent compounds useful for fluorescence microscopy and microarray analyses such as fluorescein, rhodamine and cyanine dyes and their derivatives. The labeling reagent may further contain groups that alter the affinity of the reagent for nucleic acid, such as cationic groups, minor groove binding groups and major groove binding groups, groups that alter the solubility of the reagent, or linker/spacer groups that increase the linkage distance between the components of the labeling reagent.

In a preferred embodiment, a compound is provided comprising the general structure shown in FIG. 1A, wherein D is a label selected from the group comprising detectable markers (e.g., fluorescence-emitting compounds, radioactive groups, haptens, affinity groups, immunogenic molecules, chemiluminescence-emitting compounds, proteins) and functional groups; B is a linker and may provide affinity for nucleic acid by interactions comprising electrostatic, minor groove binding, major groove binding, and intercalation; and, A is selected from the group of alkylating agents consisting of mustards and three-membered ring derivatives. B or D may also contain groups that increases the linkage distance between the label or tag and the alkylating agent. An example of such a group is polyethyleneglycol (PEG). A preferred linker segment (B) that provides affinity for nucleic acid comprises the general structure shown in FIG. 1B, wherein, R is selected from the group of alkyls and hydrogen, R' is selected from the group of alkyls and hydrogen, n is an integer from 1 to 20, m is an integer from 1 to 20, and x is an integer from 1 to 5. The labeling reagent itself may be detectable (e.g., where D is a radioactive group, a fluorescent compound or an enzyme) without further treatment. Alternatively, the labeling reagent may contain a tag that can interact, either covalently or non-covalently, with another compound which can be detected (e.g., where D is an affinity group such a biotin which can interact with a labeled streptavidin or anti-biotin antibody).

The labeled polynucleotide can be used for several purposes comprising: 1) techniques to detect specific sequences of polynucleic acids that rely upon hybridization or binding affinity of the labeled polynucleotide to target nucleic acid or protein; including dot blots, slot blots, Southern blots, Northern blots, Southwestern blot, FISH (fluorescent in situ hybridization), in situ hybridization of RNA and DNA sequences, and newly developing combinatorial techniques in which the polynucleic acid is on a "chip" or multiwell or multislot device; 2) labeling polynucleotides that are delivered to cells in vitro or in vivo so as to determine their sub-cellular and tissue location; 3) labeling oligonucleotides that are used as primers in amplification techniques such as PCR (polymerase chain reaction); 4) quantitating polynucleotides; 5) quantitating nucleases (including RNases and DNases) by fluorescence polarization or fluorescence dequenching; 6) sequencing polynucleotides; 7) directly detecting mutations; and, 8) covalently attaching reactive groups to polynucleotides.

In a preferred embodiment, a kit is provided comprising: a receptacle containing a covalently attachable labeling reagent for alkylating a polynucleotide in a single-pot reaction. Instructions for use are also provided with the kit. By the term instructions for use, it is meant a tangible expression describing the reagent concentration for at least one assay method, parameters such as the relative amount of reagent and sample to be admixed, maintenance time periods for reagent/sample admixtures, temperature, buffer conditions and the like.

Reference is now made in detail to the preferred embodiments of the invention, examples of which are illustrated in the accompanying drawings.

DETAILED DESCRIPTION

Figure 1:
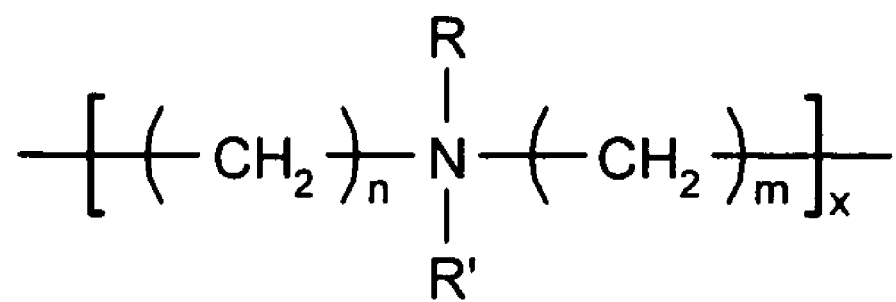
FIG. 1A-1B. The diagram in (A) illustrates the general structure for an polynucleotide labeling reagent wherein D is a label or tag, B is a linker that increases affinity of the labeling reagent for nucleic acid; and, A is a mustard or three-membered ring alkylating agent. The structure in (B) illustrates an example of a useful linker segment containing positive charge. The positive charge increases affinity of the labeling reagent for nucleic acid.

Definitions:
1. alkylation—A chemical reaction that results in the attachment of an alkyl group to the substance of interest, a nucleic acid in a preferred embodiment.
2. alkyl group—An alkyl group possesses an $sp^3$ hybridized carbon atom at the point of attachment to a molecule of interest.
3. anti-sense—oligonucleotide that has sequence complementary to specific sequence of mRNA.
4. aqueous or non-aqueous solutions—Aqueous solutions contain water. Non-aqueous solutions are made up of organic solvents
5. aziridine—A three-membered ring containing one nitrogen atom.
6. bifunctional—A molecule with two reactive ends. The reactive ends can be identical as in a homobifunctional molecule, or different as in a heterobifunctional molecule.
7. buffers—Buffers are made from a weak acid or weak base and their salts. Buffer solutions resist changes in pH when additional acid or base is added to the solution.
8. CPI moiety—Family of which alkylate double stranded DNA without cross-reactions with single stranded DNA, RNA, proteins or other nucleophile containing groups. The drug is a derivative of a naturally occurring antibiotic which binds double stranded DNA in the minor groove. All compounds in the CPI family include the functionality: 1,2,8,8a-tetrahydro-7-methylcyclopropa-[c]pyrrolo-[3,2e]indol-4(5H)-one.

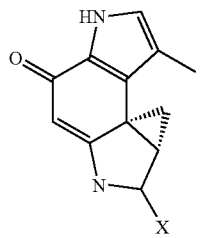

X = any molecule 9. combinatorial techniques—Techniques used to prepare and to screen extremely large pools of polynucleic acid sequences in which the sequences are in known positions on "chips", multiwell devices, multislot devices, beads, or other devices capable of segregating the nucleic acid sequences.
10. crosslinking—The chemical attachment of two or more molecules with a bifunctional reagent.
11. cyclopropane—A three-membered ring made up of all carbon atoms.
12. dot blots—Technique in which the polynucleic acid is immobilized on a nylon membrane or nitrocellulose filter before being probed with labeled polynucleic acid.
13. electrostatic interactions—The non-covalent association of two or more substances due to attractive forces between positive and negative charges.
14. enzyme—Proteins for the specific function of catalyzing chemical reactions.
15. episulfide—A three-membered ring containing one sulfur atom.
16. FISH—in situ hybridization technique in which the probe is labeled with a fluorescent marker.
17. fluorescence dequenching—technique monitoring the reappearance of fluorescent intensity when said fluorescence that had been previously quenched from having been in close proximity to another fluorescent molecule is released from close proximity to the other fluorescent molecule.
18. hapten—A small molecule that cannot alone elicit the production of antibodies to itself. However, when covalently attached to a larger molecule it can act as an antigenic determinant, and elicit antibody synthesis.
19. hybridization—Highly specific hydrogen bonding system in which guanine and cytosine form a base pair, and adenine and thymine (or uracil) form a base pair.
20. imine—A compound derived from ammonia and containing a bivalent nitrogen combined with a bivalent nonacid group, i.e. the nitrogen atom is linked to a carbon atom by a double bond (C=N—H or C=N—C) In contrast, in an amine, all atoms are covalently attached to the nitrogen via single bonds.
21. intercalating group—A chemical group characterized by planar aromatic ring structures of appropriate size and geometry capable of inserting themselves between base pairs in double-stranded DNA.
22. In Situ Hybridization—hybridization using the labeled polynucleic acid probe taking place at the site of the immobilized polynucleic acid target within the context of the cell.
23. label—Labels include reporter or marker molecules or tags such as chemical (organic or inorganic) molecules or groups capable of being detected, and in some cases, quantitated in the laboratory. Reporter molecules may be selected from the group comprising: fluorescence-emitting molecules (which include fluoresceins, rhodamines, cyanine dyes, hemi-cyanine dyes, pyrenes, lucifer yellow, BODIPY®, malachite green, coumarins, dansyl derivatives, mansyl derivatives, dabsyl drivatives, NBD flouride, stillbenes, anthrocenes, acridines, rosamines, TNS chloride, ATTO-TAG™, Lissamine™ derivatives, eosins, naphthalene derivatives, ethidium bromide derivatives, thiazole orange derivatives, ethenoadenosines, CY™Dyes, aconitine, Oregon Green, Cascade Blue, IR Dyes, Thiazole Orange PMS-127-184, Oregon Green PMS-144-19, BODIPY®-F1PMS-144-20, TAMRA, green fluorescent protein (GFP), and other fluorescent molecules), immunogenic molecules, haptens (such as digoxin), affinity molecules (such as biotin which binds to avidin and streptavidin), chemiluminescence-emitting molecules, phosphorescent molecules, oligosaccharides which bind to lectins, proteins or enzymes (such as luciferase, β-galactosidase and alkaline phosphatase), and radioactive atoms or molecules (such as $H^3$, $C^{14}$, $P^{32}$, $P^{33}$, $S^{35}$, $I^{125}$, $I^{131}$, $Tc^{99}$, and other radioactive elements). Labels also include functional groups which alter the behavior or interactions of the compound or complex to which they are attached. Functional groups may be selected from the list comprising: cell targeting signals, nuclear localization signals, compounds that enhance release of contents from endosomes or other intracellular vesicles (releasing signals), peptides (which include nuclear localization signals, polyArginine, polyHistidine, cell permeable peptides, etc.), hydrophobic or alkyl groups (such as dioleoyl and stearyl alkyl chains), and reactive groups (selected from the list comprising: carboxylic acids, amines, bromoacetamides, dibromoacetamides, PDPs, thiols, polyacids, chelators, mustards, disulfides, chelators, peptides, ligands, hydrophobic groups, and PEG).

24. labeling—Attachment of a reporter molecule or tag via a chemical bond to a compound of interest such as a nucleic acid or protein.

25. labeling reagent—A compound containing a reporter molecule, label, or tag that can be covalently attached to a nucleic acid or a protein 26. minor groove binding group—A chemical group with an affinity for the minor groove of double stranded DNA through non-covalent interactions.

27. major groove binding group—A chemical group with an affinity for the major groove of double stranded DNA through non-covalent interactions.

28. Mustards, including nitrogen mustards and sulfur mustards—Mustards are molecules consisting of a nucleophile and a leaving group separated by an ethylene bridge. After internal attack of the nucleophile on the carbon bearing the leaving group, a strained three membered group is formed. This strained ring (in the case of nitrogen mustards an aziridine ring is formed) is very susceptible to nucleophilic attack, thus allowing mustards to alkylate weak nucleophiles such as nucleic acids. Mustards which have one of the ethylene bridged leaving groups attached to the nucleophile are sometimes referred to as half-mustards. Mustard which have two of the ethylene bridged leaving groups attached to the nucleophile can be referred to as bis-mustards. Examples:
   a) nitrogen mustard—A molecule that contains a nitrogen atom and a leaving group separated by an ethylene bridge, i.e. $R_2NCH_2CH_2X$ wherein R=any chemical group, and X=a leaving group, typically a halogen.
   b) aromatic nitrogen mustard—$RR^1NCH_2CH_2X$, wherein: R=any chemical group, $R^1$=an aromatic ring, N=nitrogen, and X=a leaving group, typically a halogen.
   c) bis nitrogen mustard—$RN(CH_2CH_2X)_2$, wherein: R=any chemical group, N=nitrogen, and X=a leaving group, typically a halogen
   d) sulfur mustard—$RSCH_2CH_2X$, wherein: R=any chemical group, S=sulfur, and X=a leaving group, typically a halogen
   e) aromatic sulfur mustard—$RSCH_2CH_2X$, wherein: R=an aromatic ring, S=sulfur, and X=a leaving group, typically a halogen
   f) bis sulfur mustard—$S(CH_2CH_2X)_2$, wherein: S=sulfur and X=a leaving group, typically a halogen
   g) selenium mustard—A molecule that contains a nitrogen atom and a leaving group separated by an ethylene bridge, i.e. $R_2SeCH_2CH_2X$ wherein R=any chemical group, and X=a leaving group, typically a halogen.
   h) aromatic selenium mustard—$RR^1SeCH_2CH_2X$, wherein: R=any chemical group, $R^1$=an aromatic ring, N=nitrogen, and X=a leaving group, typically a halogen.
   i) bis selenium mustard—$RSe(CH_2CH_2X)_2$, wherein: R=any chemical group, N=nitrogen, and X=a leaving group, typically a halogen 29. Northern Blot—Technique in which the polynucleic acid (RNA) is transferred from an agarose gel to a nylon membrane or a nitrocellulose filter before being probed with labeled polynucleic acid.

30. nucleic acid—The term nucleic acid, or polynucleotide, is a term of art that refers to a polymer containing at least two nucleotides. Nucleotides are the monomeric units of nucleic acid polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA). DNA may be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. An anti-sense polynucleotide is a polynucleotide that interferes with the function of DNA and/or RNA. Antisense polynucleotides include, but are not limited to: morpholinos, 2'-O-methyl polynucleotides, DNA, RNA and the like. SiRNA comprises a double stranded structure typically containing 15-50 base pairs and preferably 21-25 base pairs and having a nucleotide sequence identical or nearly identical to an expressed target gene or RNA within the cell. Interference may result in suppression of expression. The polynucleotide can also be a sequence whose presence or expression in a cell alters the expression or function of cellular genes or RNA. In addition, DNA and RNA may be single, double, triple, or quadruple stranded. Double, triple, and quadruple stranded nucleic acid may contain both RNA and DNA or other combinations of natural and/or synthetic nucleic acids.

31. oligonucleotide—A polynucleic acid with 50 or fewer base-sugar-phosphate groups.

32. oxirane—A three-membered ring containing one oxygen atom, also called an epoxide.

33. photochemical—Refers to a reaction that requires a light source for initiation of reaction.
34. R-chloride—The aromatic nitrogen mustard 4-[(2-chloroethyl)-methylamino]-benzylamine.
35. R-aldehyde—The aromatic nitrogen mustard 4-[(2-chloroethyl)-methylamino]-benzaldehyde.
36. radioactiveprotein—a molecule made up of 2 or more amino acids. The amino acids may be naturally occurring, recombinant or synthetic.
37. Radioactive detectable markers are characterized by one or more radioisotopes of phosphorous, iodine, hydrogen, carbon, cobalt, nickel, and the like. Detection of radioactive reporter molecules is typically accomplished by the stimulation of photon emission from crystalline detectors caused by the radiation, or by the fogging of a photographic emulsion.
38. R-aldehyde—The aromatic nitrogen mustard 4-[(2-chloroethyl)-methylamino]-benzaldehyde
39. salts—Salts are ionic compounds that dissociate into cations and anions when dissolved in solution. Salts increase the ionic strength of a solution, and consequently decrease interactions between polynucleic acids with other cations.
40. single-pot reaction—A reaction set up to take place after all of the reagents necessary to perform covalent attachment are placed in contact with each other in a receptacle, without further steps. Also called a one-pot reaction.
41. siRNA—SiRNA comprises a double stranded nucleic acid structure typically containing 15-50 base pairs and preferably 21-25 base pairs and having a nucleotide sequence identical or nearly identical to an expressed target gene or RNA within the cell.
42. slot Blots—Technique in which the polynucleic acid is immobilized on a nylon membrane or nitrocellulose filter using a slot blot apparatus before being probed with labeled polynucleic acid.
43. Southern Blot—Technique in which the polynucleic acid (nucleic acid) is transferred from an agarose gel to a nylon membrane or a nitrocellulose filter before being probed with labeled polynucleic acid.
44. Southwestern Blot—Technique in which protein is transferred from an acrylamide gel to a nylon membrane or a nitrocellulose filter before being probed with labeled polynucleic acid.

One can determine whether or not a particular compound is suitable for the present invention by comparing the candidate compound with successful compounds illustrated in the examples. A suitable alkylating compound will alkylate a target molecule in a one-pot reaction. The examples demonstrate suitable methods and preparation of compounds for successful alkylation of nucleic acid. A compound suitable for use with the present invention minimally consists of an alkylating group and a label (components A and D below). Suitable compounds may also contain a spacer group (component S below) or an additional component to increase affinity of the labeling reagent for nucleic acid or alter the charge of the labeling reagent (component B below):

A—Alkylating group—chemical functionalities that are electrophilic, allowing them to become covalently attached to compounds bearing a nucleophilic group. Alkylating reagents include mustards (nitrogen mustards and sulfur mustards ); and three-membered rings (aziridines, oxiranes, cyclopranes, activated cyclopropanes, and episulfides), including charged three-membered rings.

D—Label: reporter group (detectable marker) or functional group.

reporter group—a chemical moiety attached to the compound for purposes of detection. The reporter molecule may be fluorescent, such as a rhodamine or flourescein derivative or a cyanine dye. The reporter molecule may be a hapten, such as digoxin, or a molecule which binds to another molecule such as biotin which binds to avidin and streptavidin or-oligosaccharides which bind to lectins. The reporter molecule may be a protein or an enzyme such as alkaline phosphatase. The reporter molecule may also be or contain radioactive atoms such as $H^3$, $C^{14}$, $P^{32}$, $P^{33}$, $S^{35}$, $I^{125}$, $I^{31}$, $Tc^{99}$, and other radioactive elements.

functional group—a group that adds functionality. This group comprises: reactive groups, charged groups, alkyl groups, polyethyleneglycol, ligands, and peptides. A reactive group is capable of undergoing further chemical reactions. Reactive groups include, but are not limited to: alkylating groups (including mustards and three-membered rings), amines, alcohols, thiols, isothiocyanates, isocyanates, acyl azides, N-hydroxysuccinimides, sufonyl chlorides, aldehydes, epoxides, carbonates, imidoesters, carboxylates, alkylphosphates, arylhalides (such as difluoro-dinitrobenzene), iodoacetamides, maleimides, aziridines, acryloyl chlorides, flourobenzes, disulfides, succinamides, carboxylic acids, and activated carboxylic groups.

S—Linker/Spacer—a connection, typically between the alkylating group and the label, selected from the group comprising: alkanes, alkenes, esters, ethers, glycerol, amide, saccharides, polysaccharides, heteroatoms such as oxygen, sulfur, or nitrogen, and molecules that are cleavable under physiologic conditions such as a disulfide bridges or enzyme-sensitive groups. The spacer may bear a net positive charge, or be any of the following: minor groove binders, major groove binders, intercalating groups, or other proteins or groups that increase the affinity of the compound for nucleic acid. The spacer may alleviate possible molecular interference by separating the reporter molecule from the alkylating compound or nucleic acid after alkylation. The spacer may also contain a group that increases the linkage distance between the label or tag and the alkylating agent (A). The spacer may also increase the aqueous solubility of the labeling reagent.

B—Affinity group—a group that increases affinity of the reagent for nucleic acid or alters the overall charge of the labeling reagent. The affinity group can be attached to the alkylating group, to the label or to the linker/spacer. Alternatively, the affinity group may be incorporated into the linker/spacer. The affinity group may bear a net positive charge or be any of the following: minor groove binders, major groove binders, intercalating groups, or other proteins or groups that increase the affinity of the compound for nucleic acid. If the other components of the labeling reagent combine to bear a net positive charge, the affinity group may bear a net negative charge, provided the net charge of the reactive species of the labeling reagent is greater than zero. The affinity group may also increase the aqueous solubility of the labeling reagent.

In order for a labeling reagent to be effective, we have found that it is important that the compound have affinity for nucleic acid when the labeling occurs. In other words, the reactive species must have affinity for nucleic acid. This feature serves to increase the affinity of the reagent for the nucleic acid being modified, allowing a functional amount of labeling to occur.

For example, a net charge greater than zero on the labeling reagent when the labeling occurs can provide affinity for nucleic acid. In this example, if the label group carries negative charge, then the linker, alkylating group and affinity group must bear enough combined net positive charge such that the net charge of the reactive species is greater than zero. Thus, the net charge on a labeling reagent can be equal to or greater than zero. A net neutral labeling reagent (charge equal to zero) is effective if the reagent becomes positively charged during the alkylation reaction. As an example, for the compound shown in FIG. 4C, the aromatic nitrogen mustard forms a positively charged aziridine intermediate. (FIG. 4D) during the alkylation reaction. FIG. 4C is therefore an effective labeling reagent. If the nitrogen mustard contained a secondary amine (as in FIG. 4E), the intermediate (FIG. 4F) would not gain a positive charge. Thus, for a secondary amine-containing nitrogen mustard, where affinity for nucleic acid is based on charge, the net positive charge, on the labeling reagent would need to be greater than zero.

Any of a large number of nucleic acid sequences may be employed in accord with this invention for use as probes in the detection of target molecules. Included, for example, are target sequences in both RNA and DNA, as are the polynucleotide sequences that characterize various viral, viroid, fungal, parasitic or bacterial infections, genetic disorders or other sequences in target molecules that are desirable to detect. The described labeling reagents can also be used to label both single stranded and double stranded oligonucleotides, including siRNA. Probes may be of synthetic, semi-synthetic or natural origin. Probe molecules include both polyribonucleotides and polydeoxyribonucleotides.

EXAMPLES

Synthesis

The synthetic methodology used to prepare the labeling reagents of the invention is described below. The structures of several labeling reagents are illustrated in FIG. 3.

Example 1

Synthesis of Labeling Reagents. The synthetic methodology used to prepare the labeling reagents of the invention is described below and in U.S. Pat. No. 6,262,252 incorporated herein by reference.

Example 2

2A) Preparation of 3-bromo-1-(trifluoroacetamidyl)propane. To a solution of 3-bromopropylamine (2.19 g, 10.0 mmol, Aldrich Chemical Co., Milwaukee, Wis.) and triethyl amine (1.67 mL, 12.0 mmol, Aldrich Chemical Co.) in 60 mL methylene chloride at 0° C. in a 200 mL roundbottom flask equipped with a addition funnel was added trifluoroacetic anhydride (1.69 mL, 12.0 mmol, Aldrich Chemical Co.) in 60 mL methylene chloride over a period of 20 minutes. The reaction was stirred overnight, washed 1×10 mL 2% bicarbonate, 1×10 mL water, and dried over magnesium sulfate. Removal of solvent yielded 2.07 g (88.5%) product as amorphous crystals. $H^1$-NMR (CDCl$_3$): δ 3.55 (m, 2H), 3.45 (m, 2H), 2.17 (m, 2H).

2B) N,N-dimethyl-N-[N'-(tert-butoxycarbonyl)-3-aminopropylamine]. 3-dimethylaminopropylamine (251 µL, 204 mg, 2.00 mmol, Aldrich Chemical Co.) was combined with diisopropylamine (348 µL, 2.00 mmol, Aldrich Chemical Co.) in 2 mL tetrahydrofuran. BOC-ON (542 mg, 2.20 mmol, Aldrich Chemical Co.) was added to the stirring reaction mixture. The reaction mixture was stirred at room temperature for 12 hours. Following removal of THF on a rotary evaporator the residue was dissolved in 30 mL diethyl ether, washed 3×2N NaOH, and dried over MgSO$_4$. Solvent removal yielded 359 mg (88.7%) product as a colorless oil. $H^1$-NMR (CDCl$_3$): δ 5.16 (bs, 1H), 3.76 (m, 2H), 2.30 (m, 2H), 2.21 (s, 6H), 1.65 (m, 2H), 1.44 (s, 9H).

Figure 2:
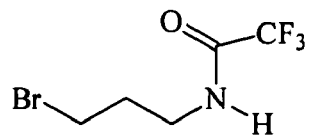
FIGS. 2A-2E. Illustrations of the chemical structures for:
A. 3-bromo-1-(trifluoroacetamidyl)propane.
B. N,N-dimethyl-N-[N'-(tert-butoxycarbonyl)-3-aminopropylamine].
C. N-[N'-(tert-butoxycarbonyl)-3-aminopropyl]-N,N-dimethyl-3-aminopropylammonium salt.
D. N-[N'-{4-[(2-chloroethyl)-methylamino]-benzylamine}-3-aminopropyl]-N,N-dimethyl-3-aminopropylammonium salt.
E. the nucleic acid labeling reagent LABEL-IT®-Cyanine3.
Figure 2:
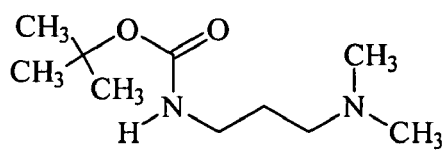
Figure 2:
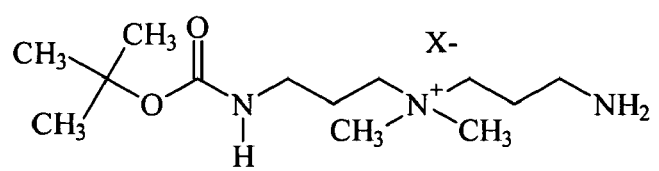
Figure 2:
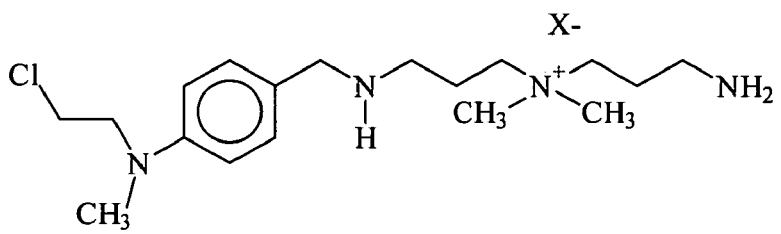
Figure 2:
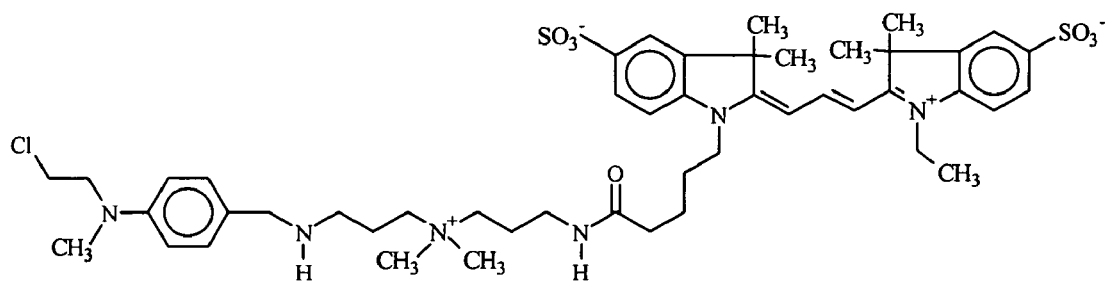

2C) N-[N'-(tert-butoxycarbonyl)-3-aminopropyl]-N,N-dimethyl-3-aminopropylammonium carbonate. FIG. 2B (344 mg, 1.70 mmol) and FIG. 2A (433 mg, 1.85 mmol) were combined in 250 µL anhydrous dimethylformamide (DMF), and incubated at 55° C. for 48 hours. Product was precipitated from the reaction mixture by the addition of diethyl ether. Product was dried under vacuum yielding 686 mg (92.5%) product as a colorless oil. $H^1$-NMR (D$_2$O): δ 7.95 (s, 1H), 3.45 (m, 2H), 3.35 (m, 4H), 3.20 (m, 2H), 3.10 (s, 6H), 2.10 (m, 2H), 1,45 (s, 9H). The triflouroacetamide group was cleaved by dissolving the reaction product (179 mg, 0.409 mmol) in 1.0 mL methanol and 0.5 mL water. Sodium carbonate (173 mg, 4.09 mmol) was added and the reaction was stirred at room temperature for 12 hours. The carbonate was removed by centrifugation. Product was dissolved in methanol and precipitated by the addition of diethyl ether yielding 93.5 mg (66.5%) product as a colorless solid. TLC: silica gel; water/acetic acid/ethyl acetate; 2/2/1; Rf=0.61, developed using Dragendorff's Reagent. $H^1$-NMR (CD$_3$OD): δ 3.37 (m, 4H), 3.15 (m, 8H), 2.73 (m, 2H), 1.94 (m, 4H), 1.44 (s, 9H).

2D) N-[N'{(4-[(2-chloroethyl)-methylamino]-benzylamine}-3-aminopropyl]-N,N-dimethyl-3-aminopropylammonium tetra-trifluoroacetate salt. FIG. 2C (123 mg, 0.382 mmol) and 4-[(2-chloroethyl)-methylamino]-benzaldehyde (75.5 mg, 0.382 mmol, kindly provided by V. V. Vlassov, Institute of Bioorganic Chemistry, Siberian Division of the Russian Academy of Sciences, Novosibirsk) were dissolved in 9 mL methanol. Sodium cyanoborohydride (24.0 mg, 0.381 mmol, Aldrich Chemical Co.) was added. The reaction was stirred at room temperature for 18 hours. Solvent was removed from the reaction mixture, the residue was dissolved in TFA, and incubated for 20 minutes at room temperature to remove the BOC protecting group. The TFA was evaporated under a stream of nitrogen, and the residue was purified via HPLC (C-18: acetonitrile/0.1% TFA) to yield 85.0 (27.9%) as a yellow oil. TLC: silica gel; dimethylformamide/acetic acid/water; 1/2/2; Rf=0.31.

2E) LABEL-IT®-Cyanine3. FIG. 2D (100 mg, 0.125 mmol) and Cyanine3 mono NHS ester (100 mg, 0.130 mmol, Amersham Biosciences) were dissolved in 1.0 mL DMF. Diisopropylethylamine (64.5 mg, 0.5 mmol) was added, and the reaction was stirred at room temperature for 2 hours. The product was purified by HPLC using: column (Aquasil C-18, 250×20 mm, Keystone Scientific), and mobile phase (methanol containing 0.1% trifluoroacetic acid: 15 mL/min). Final product was identified by mass spectrometry (PE Sciex 150EX, Perkin-Elmer Biosciences) molecular ion (M$^+$, 953 amu).

Example 3

Many different labeling reagents can be synthesized according to the procedures described above. For instance, many different labeling reagents can be made by attaching a desired label or tag to compound FIG. 2D.

Figure 3A:
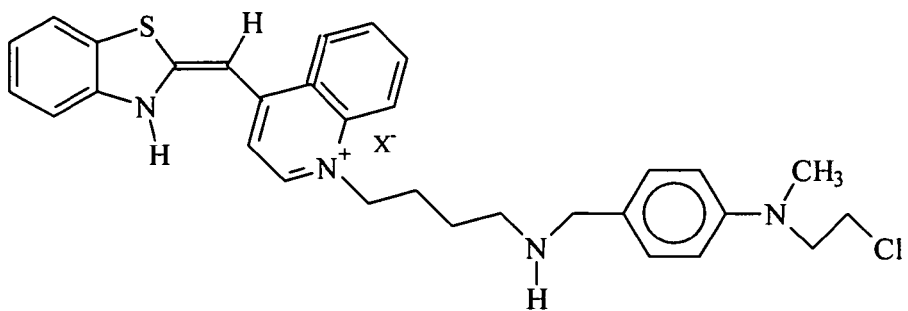
FIG. 3A. Illustrations of labeling reagents having fluorescent labels. (i) LABEL-IT®-Thiazole Orange. (ii) LABEL-IT®-Cyanine5. (iii) LABEL-IT®-Cyanine3.
Figure 3A:
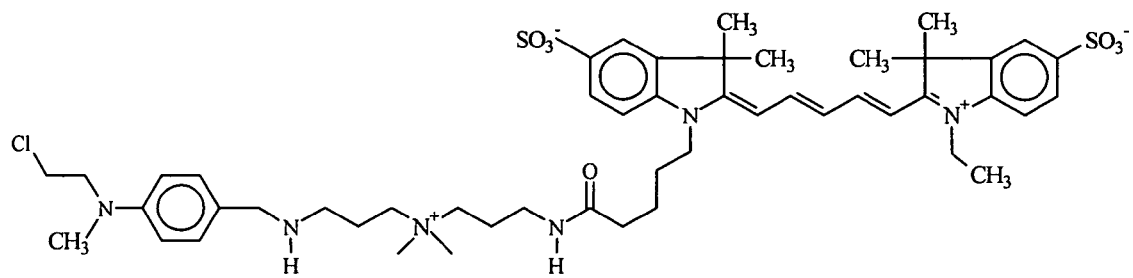
Figure 3A:
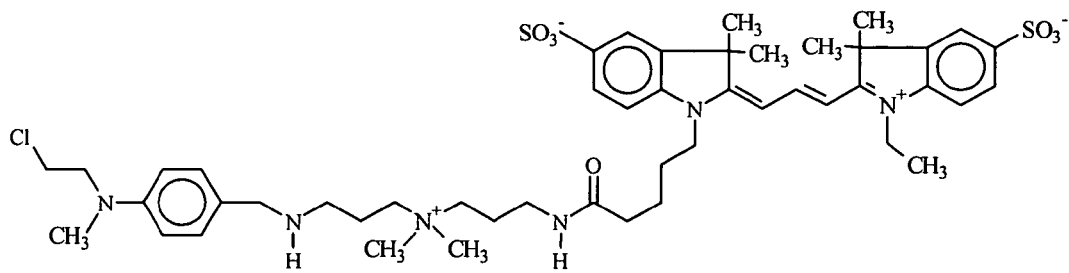

FIG. 3A illustrates the structures for a number of labeling reagents containing fluorescent dyes (fluorochromes/fluorophores): The LABEL-IT®-Thiazole Orange labeling reagent incorporates a minor groove binding linker to increase affinity of the labeling reagent for nucleic acid. This labeling reagent was prepared from 4-[(2-chloroethyl)-methylamino]-benzldehyde and thiazole orange iodide. The product was purified by HPLC, and was confirmed using mass spectrometry. The molecular ion ($M^+$) was found at 529 amu. Plasmid DNA was incubated for 1 h at 37° C. in 20 mM MOPS buffer pH 7.5 along with the LABEL-IT®-Thiazole Orange reagent. Ratios of DNA to reagent ranged from 0.2:1 to 1:1. Reactions were purified by ethanol precipitation and analyzed on a 1% agarose gel. Incorporation of the reagent was verified by visible staining prior to ethidium bromide staining and by retarded migration of the labeled DNA in the gel. The LABEL-IT®-Thiazole Orange labeling reagent also represent an example of a labeling reagent that is only fluorescent in double strand nucleic acid. Therefore, such labeling reagents may be useful for oligo array or other procedures where fluorescence only from hybridized nucleic acid is desirable. Also shown in FIG. 3A are LABEL-IT®-Cyanine5 and LABEL-IT®-Cyanine3 labeling reagents.

Figure 3B:
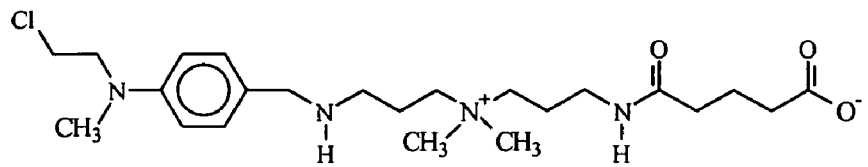
FIG. 3B. Illustrations of labeling reagents having functional groups. (i) LABEL-IT®-Carboxylic acid. (ii) LABEL-IT®-Amine (iii) LABEL-IT®-Diamine. (iv) LABEL-IT®-Triamine. (v) LABEL-IT®-Tetra-amine. (vi) LABEL-IT®-Hexamine. (vii) LABEL-IT®-Bromoacetamide. (viii) LABEL-IT®-Dibromoacetamide. (ix) LABEL-IT®-PDP. (x) LAB EL-IT®-Cysteine-PDP.
Figure 3B:
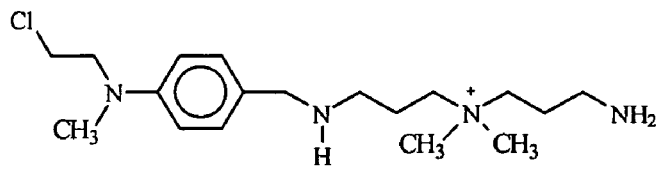
Figure 3B:
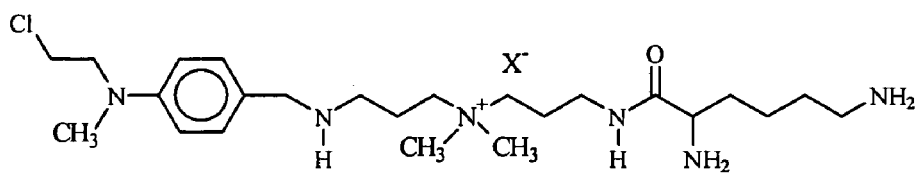
Figure 3B:
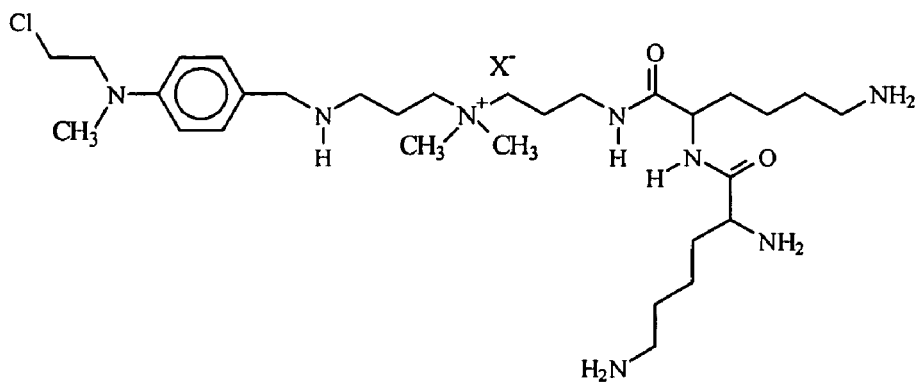
Figure 3B:
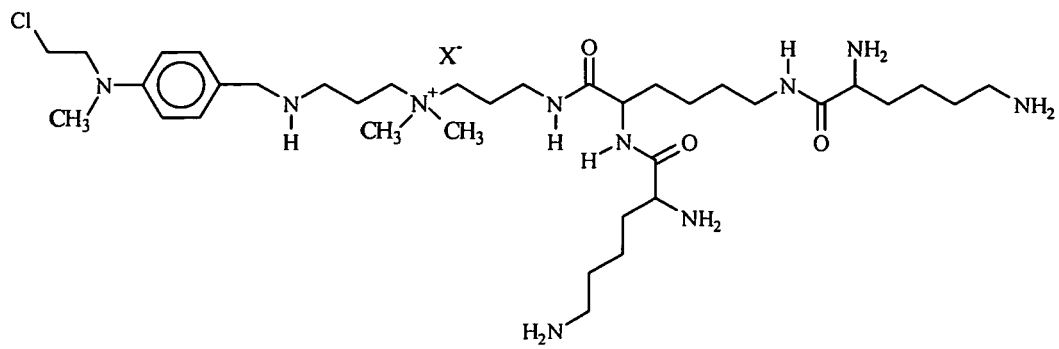
Figure 3B:
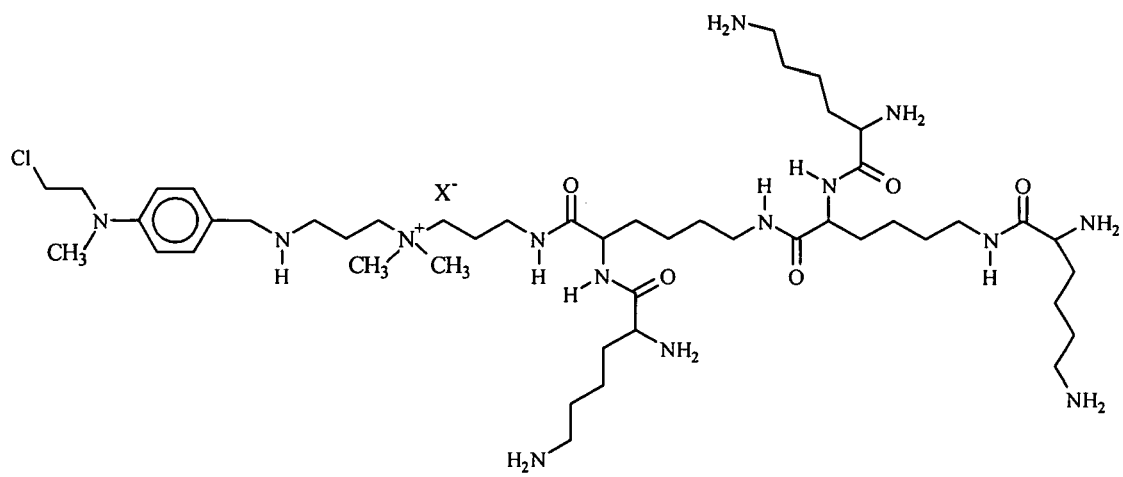
Figure 3B:
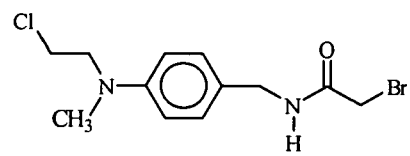
Figure 3B:
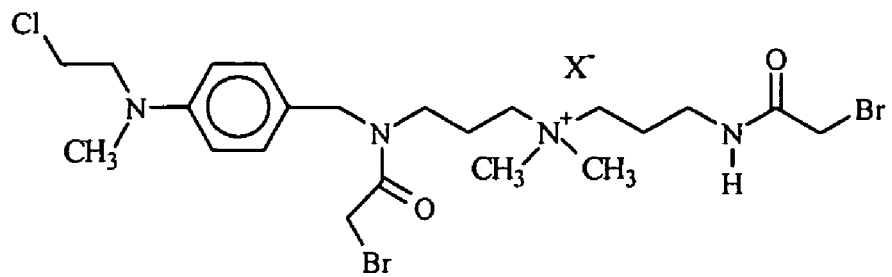
Figure 3B:
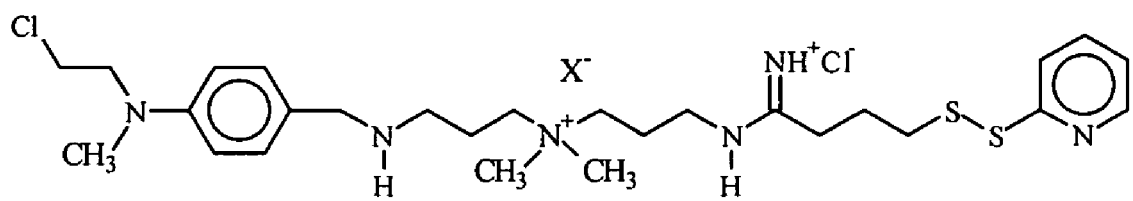
Figure 3B:
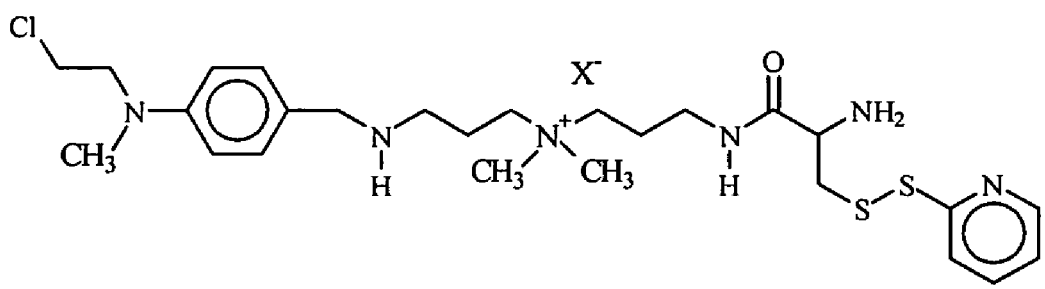

FIG. 3B illustrates the structures for a number of labeling reagents containing reactive groups.

LABEL-IT®-Carboxylic acid can provide a means for attachment of amine containing compounds to the labeling reagent.

LABEL-IT®-Amine can add positive charge to a nucleic acid or provide a means for attachment of primary amine reactive compounds to the labeling reagent or to labeled nucleic acid.

LABEL-IT®-Diamine, LABEL-IT®-Triamine, LABEL-IT®-Tetraamine, LABEL-IT®-Hexamine can add positive charge to a nucleic acid or provide a means for attachment of primary amine reactive compounds to the labeling reagent or to labeled nucleic acid. The multiple positive charges can allow condensation of DNA by polycations at low charge neutralization levels. LABEL-IT®-Bromoacetamide and LABEL-IT®-Dibromoacetamide can provide for attachment of thiol containing compounds or surfaces to the labeling reagent or to a labeled nucleic acid.

LABEL-IT®-PDP and LABEL-IT®-Cysteine-PDP can provide for attachment to bromoacetamides and malemides and thioesters for intermolecular disulfide bond formation.

Figure 3C:
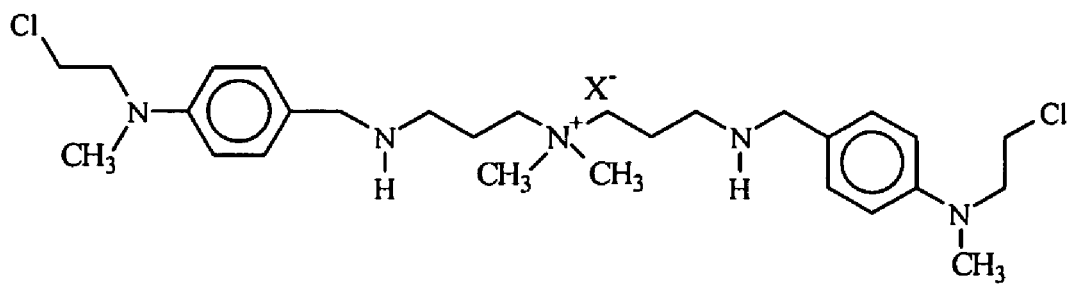
FIG. 3C. Illustrations of labeling reagents having multiple alkylation centers. (i) Di-LABEL-IT®. (ii) Tri-LABEL-IT®.
Figure 3C:
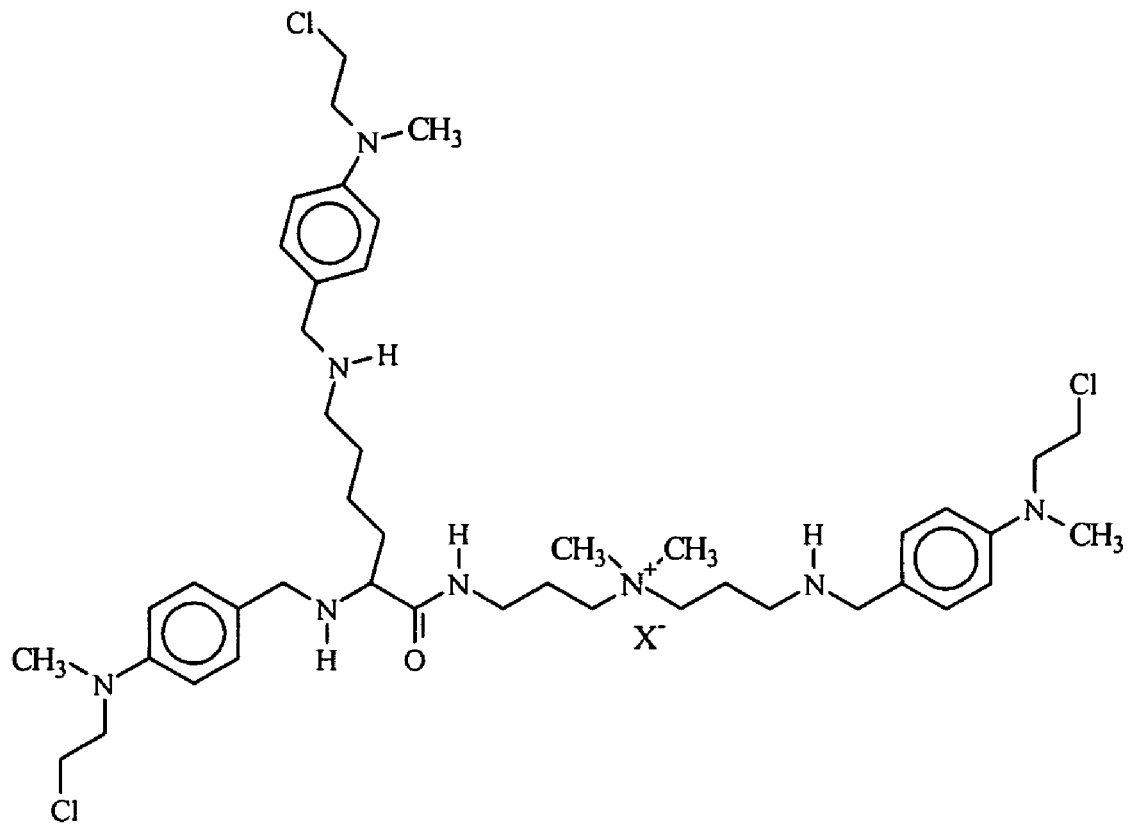

FIG. 3C illustrates the structures for two labeling reagents containing multiple alkylating groups. Di-LABEL-IT® and Tri-LABEL-IT® can be used to crosslink nucleic acid and potentially as anticancer drugs.

Figure 3D:
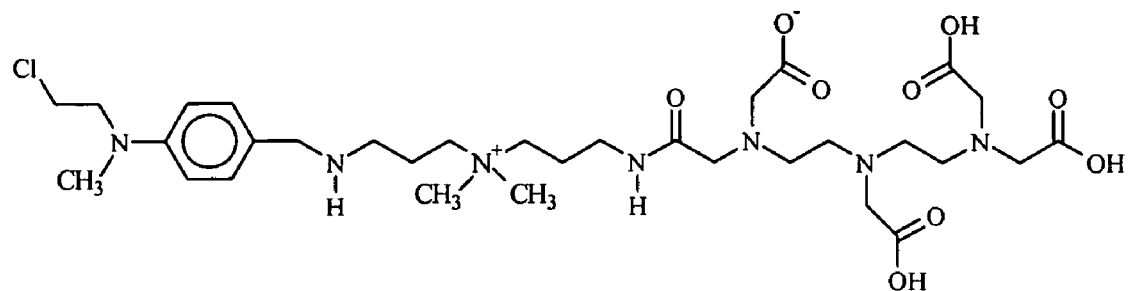
FIG. 3D. Illustrations of labeling reagents having chelators. (i) LABEL-IT®-Polyacid chelator. (ii) LABEL-IT®-Chelator.
Figure 3D:
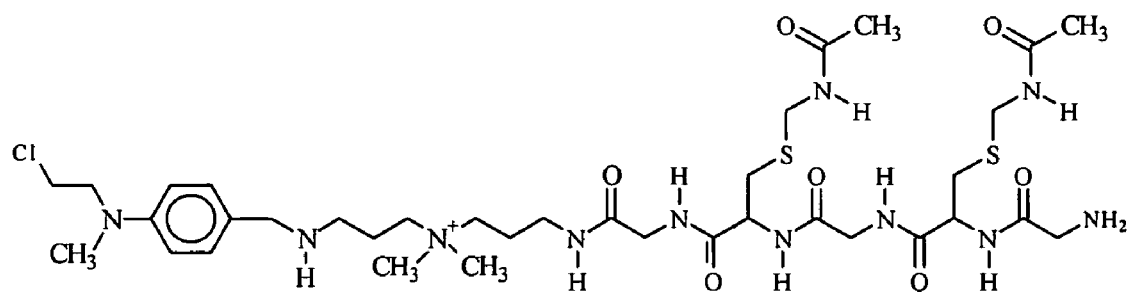

FIG. 3D illustrates the structures for two labeling Keagents containing chelator functionality: LABEL-IT®-Polyacid chelator, and LABEL-IT®-Chelator. These labeling reagent are expected to chelate lanthanides and potentially calcium. Because of its positive charge, LABEL-IT®-Chelator is expected to be a much more efficient labeling reagent than LABEL-IT®-Polyacid chelator.

Figure 3E:
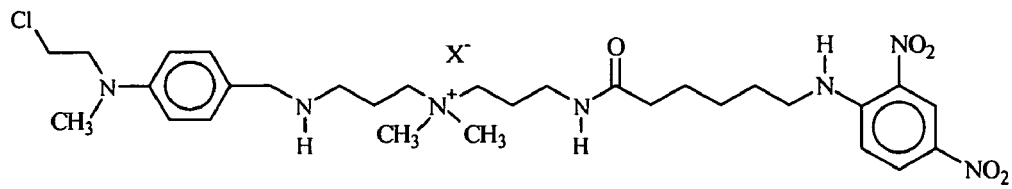
FIG. 3E. Illustrations of labeling reagents having affinity molecule groups. (i) LABEL-IT®-DNP. (ii) LABEL-IT®-Hexaethyleneglycol-Biotin (iii) LABEL-IT®-PEG$_{3400}$-Biotin.
Figure 3E:
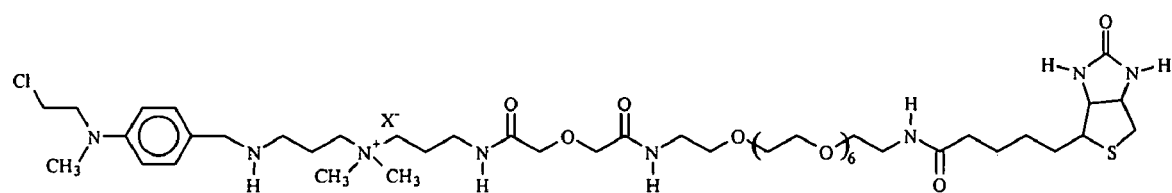
Figure 3E:
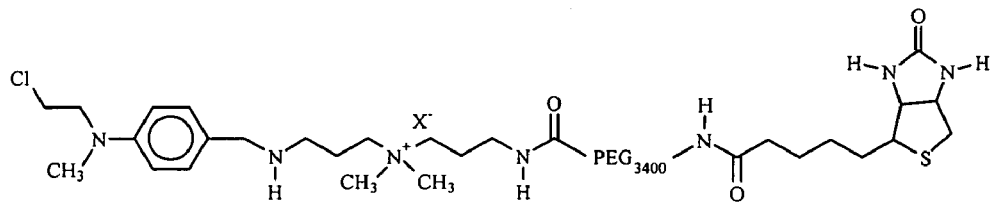

FIG. 3E illustrates the structures for a number of labeling reagents containing affinity molecule groups: LABEL-IT®-DNP, LABEL-IT®-Hexaethyleneglycol-Biotin, and LABEL-IT®-PEG$_{3400}$-Biotin. The hexaethyleneglyco and PEG linkers separate the affinity molecule group from the alkylating group and therefore the nucleic acid. This separation may enhance binding of secondary compounds to these groups. Labeling reagents that contain multiple affinity molecule groups can easily be envisioned.

Figure 3F:
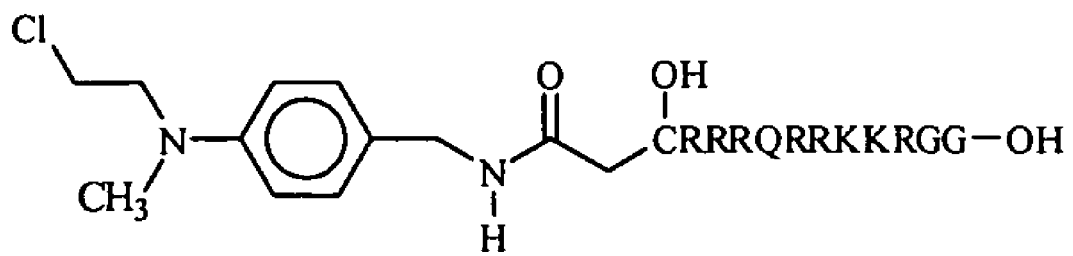
FIG. 3F. Illustrations of labeling reagents having peptides. (i) LABEL-IT®-TAT (ii) LABEL-IT®-Polyhistidine. (iii) LABEL-IT®-NLS (nuclear localization signal).
Figure 3F:
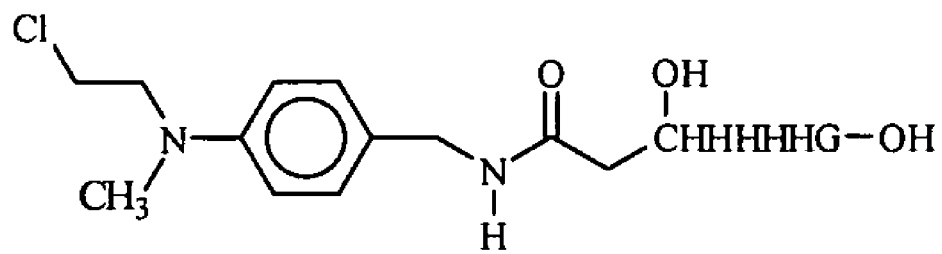
Figure 3F:
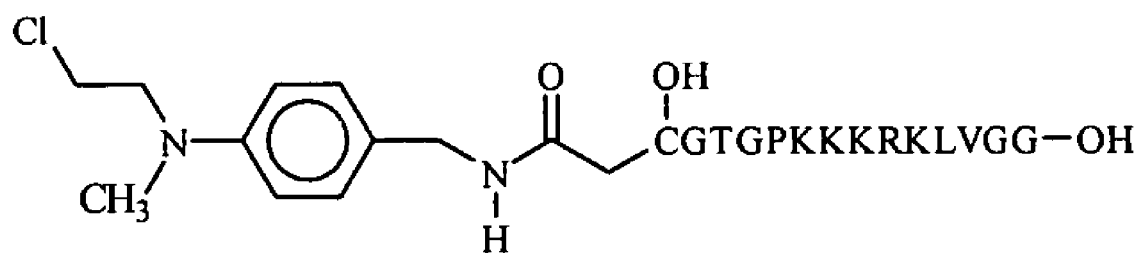

FIG. 3F illustrates the structures for a number of labeling reagents containing peptides. LABEL-IT®-TAT (HIV TAT peptide) contains the membrane permeable TAT peptide. This peptide has been reported to facilitate transport compounds to which it is attached across biological or synthetic membrane bilayers. LABEL-IT®-Polyhistidine can be used to facilitate purification of nucleic acid to which it is attached or to provide pH dependent charge on the nucleic acid. LABEL-IT®-NLS (nuclear localization signal) can be used to provide nuclear targeting to nucleic acid to which it is attached. Because each of these peptide labels happens to be positively charged, positive charge is not required within the linker to provide affinity for nucleic acid.

Figure 3G:
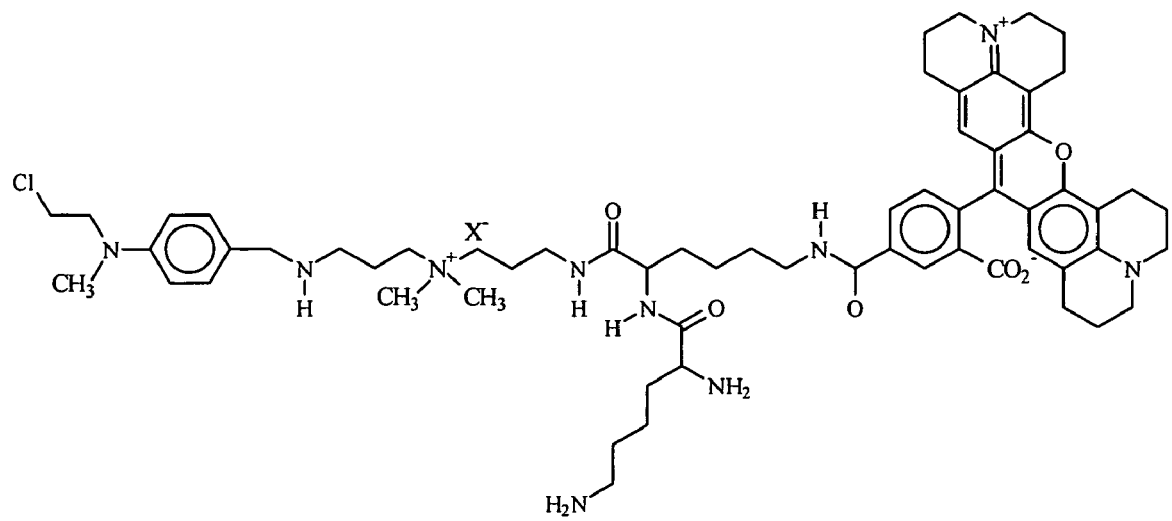
FIG. 3G. Illustrations of labeling reagents having multifunctional labels. (i) LABEL-IT®-Diamine-Rhodamine. (ii) LABEL-IT®-Rhodamine-Hexaethyleneglycol-Biotin.
Figure 3G:
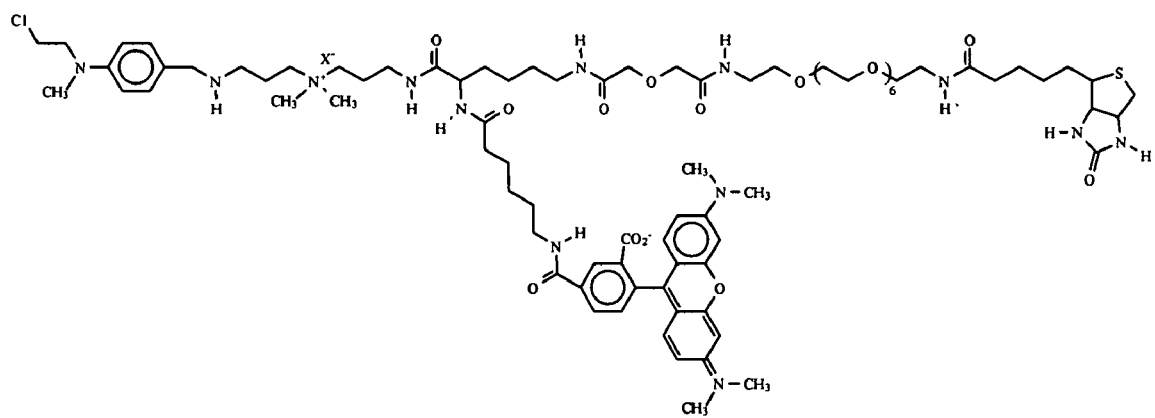

FIG. 3G illustrates the structures for two labeling reagents containing multifunction labels. LABEL-IT®-Diamine-Rhodamine is fluorescent and contains primary amines. LABEL-IT®-Rhodamine-Hexaethyleneglycol-Biotin is fluorescent and contains an affinity molecule group separated from the fluorescent group and the nucleic acid by a spacer.

Figure 3H:
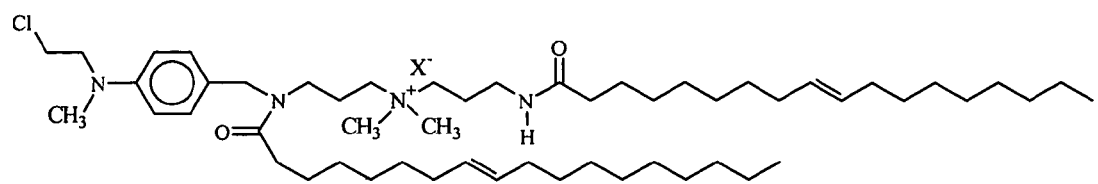
FIG. 3H. Illustrations of labeling reagents having Hydrophobic groups. (i) LABEL-IT®-Dioleoyl. (ii) LABEL-IT®-Stearyl.
Figure 3H:
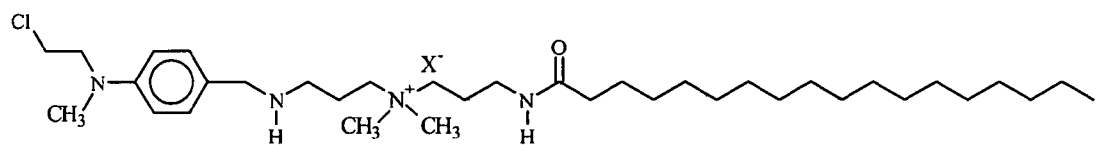

FIG. 3H illustrates the structures for two labeling reagents containing hydrophobic groups: LABEL-IT®-Dioleoyl and LABEL-IT®-Stearyl The hydrophobic groups may impart membrane activity or may be used to attach nucleic acid to membranes or to reverse phase beads and surfaces.

The inclusion of different linkers can affect the usefulness of labeling reagents. The labeling reagent shown in FIG. 3G(ii) has a hexathylene glycol spacer. The labeling reagent shown in FIG. 3E(iii) has a PEG spacer. Incorporation of spacers can decrease quenching of fluorescent labels or decrease interactions between the label and the nucleic acid.

These examples represent a range of labels that can incorporated into labeling reagents according to the invention.

Example 4

Labeling Reagents can be covalently attached to double stranded DNA (dsDNA). By means of the procedure set forth below, covalent attachment of the labeling reagents to double stranded plasmid DNA (pDNA) is demonstrated. Detectable non-radioactive labels (fluorescein, rhodamine) coupled to nitrogen mustards (see synthesis section) were covalently attached to nucleic acids. Unincorporated labeling reagent is removed from labeled DNA by ethanol precipitation in 0.5 M NaCl.

(1) Materials
 1. pDNA (3.3 µg/µL pCIluc; prepared according to Danko et al 1997)
 2. LABEL-IT®-Carboxy-X-Rhodamine
 3. LABEL-IT®-Fluorescein
 4. Hepes buffer (100 mM, pH 7.5)
 5. NaCl (5 M aqueous solution)
 6. Ethanol (100%, Pharmco, Brookfield, Conn.)
 7. 70% Ethanol
 8. Photo-documentation camera equipped with a photo-documentation hood (FB-PDC-34 and FB-PDH-1314, FisherBiotech, Pittsburgh, Pa.)
 9. Ethidium bromide (Acros Organics, Pittsburgh, Pa.)

(2) Reaction Protocol
 0. For negative control purposes 5.0 µg portions each of LABEL-IT®-Carboxy-X-Rhodamine and LABEL-IT®-Fluorescein were incubated in 200 µL Hepes buffer for 48 h to hydrolyze the nitrogen mustard.

These samples are used as negative controls; they no longer contain an alkylating group.
1. LABEL-IT® -Carboxy-X-Rhodamine (1.0 µg), LABEL-IT®-Fluorescein (5 µg), hydrolyzed LABEL-IT®-Carboxy-X-Rhodamine (1.0 µg), and hydrolyzed LABEL-IT®-Fluorescein (5.0 µg) were combined with plasmid DNA (5 µg) in 150 µL Hepes buffer. The reactions were vortexed to mix.
2. The reactions were incubated at 37° C. for 1 hour.
3. 15 µL 5 M NaCl was added to each tube, the solutions was vortexed to mix, and 2 volumes ethanol was added.
4. The reactions were incubated at −10° C. for 10 minutes, and centrifuged at 12000 rpm for 5 minutes. The supernatant was decanted, and the pellets were washed with 70% ethanol.
5. The pellets were dissolved in 100 µL Hepes buffer. 0.4 µg labeled DNA from each reaction was run on a 1% agarose gel.
6. A photograph was taken 0n a UV lightbox prior to ethidium bromide staining (3 second exposure), and after ethidium staining (1 second exposure).

(3) Results

The covalent attachment of the labeling reagents is demonstrated by visualization of DNA bands without ethidium bromide staining. The labeled DNA was visible due to the fluorescence of the covalently attached rhodamine, and fluorescein respectively. The unlabeled control plasmid was not visible, nor was the plasmid DNA incubated with hydrolyzed LABEL-IT®-Carboxy-X-Rhodamine and LABEL-IT®-Fluorescein. Thus when the mustard moiety on the labeling reagents is hydrolyzed, no labeling of DNA is observed.

The integrity of the labeled plasmids was demonstrated by comparing the ratio of supercoiled to relaxed circular plasmid DNA in the unlabeled controls with that of the labeled plasmids. For this analysis, DNA was visualized by ethidium bromide staining. Any nicking would result in an increase in relaxed circular plasmid DNA. Analysis of the photograph revealed nicking levels to be low.

Example 5

Labeling reagents can be covalently attached to single stranded DNA (ssDNA).
(1) Materials: M13 bateriophage M13mp18 ssDNA (Panvera Corporation, Madison, Wis.)
(2) Procedure and Results: The ssDNA was labeled using LABEL-IT®-Carboxy-X-Rhodamine according to example 1 using a 30 minute incubation period at 37° C., and a labeling reagent to DNA ratio of 0.2:1. The labeled ssDNA was analyzed by agarose gel electrophoresis of 1.0 µg DNA per lane.
(3) Results: Incorporation of the labeling compounds was demonstrated by the observed fluorescence of labeled ssDNA and the absence of fluorescence of unlabeled ssDNA prior to ethidium staining. The integrity of the labeled DNA was demonstrated by comparing the ethidium stained unlabeled control ssDNA with the ethidium stained labeled ssDNA.

Example 6

Labeling Reagents can be covalently attached to RNA
(1) Materials
1. calf liver tRNA (Boehringer Mannheim Corporation, Indianapolis, Ind.)
2. 900 b in vitro transcribed RNA (0.3 µg/mL)
3. LABEL-IT®-Carboxy-X-Rhodamine
(2) Procedure: The RNAs were labeled using LABEL-IT®-Carboxy-X-Rhodamine according to example 1 using a 30 minute incubation period at 37° C., and a labeling reagent to RNA ratio of 0.2:1. The labeled RNAs were analyzed by agarose gel electrophoresis of 1.0 µg RNA per lane.
(3) Results: Covalent attachment of the labeling reagent to the RNAs was evident because RNA incubated with reagent showed visible fluorescence without ethidium bromide staining. The labeled RNA bands and the unlabeled RNA bands both migrated to an equal extent in the agarose gel, thereby demonstrating that the covalent attachment of the labeling reagent does not harm the RNA.

Example 7

Labeling reagents can be covalently attached to linear double stranded DNA.
(1) Materials: λ DNA/hind III fragments (Life Technologies Inc., Gaithersburg, Md.)
(2) Procedure: The linearized λ DNA was labeled using LABEL-IT®-Carboxy-X-Rhodamine according to example 1 using a 30 minute incubation period at 37° C., and a labeling reagent to DNA ratio of 0.2:1. The labeled linearized dsDNA was analyzed by agarose gel electrophoresis of 1.0 µg DNA per lane.
(3) Results: Covalent attachment of the labeling reagent to the linearized dsDNAs was evident because linearized dsDNA incubated with reagent showed visible fluorescence prior to ethidium bromide staining. The labeled linearized dsDNA bands and the unlabeled linearized dsDNA bands both migrated to an equal extent in the agarose gel, thereby demonstrating that the covalent attachment of the labeling reagent does not harm the linearized ds DNA.

Example 8

Incorporation of labeling reagents onto the polynucleotide is proportional to the amount of labeling reagent used. The extent of labeling reagent incorporation into the polynucleotide can be controlled by regulating the ratio of labeling reagent to polynucleotide.
(1) Experimental Protocol: pDNAs (pCIluc) were labeled according to the procedure in example 1 using LABEL-IT®-Carboxy-X-Rhodamine as the labeling reagent. DNA was labeled at the following weight to weight ratios (labeling reagent:DNA): (0.01:1), (0.02:1), (0.05:1), (0.10:1), (0.20:1), (0.50:1), and (1:1). 0.2 µg DNA samples were analyzed on an agarose gel. The remaining portion of labeled DNA was analyzed on a Beckman DU6 UV/visible spectrophotometer (Beckman Instruments, Inc. Arlington Heights, Ill.).
(2) Results: Extent of incorporation was observed by visualization of an agarose gel prior to ethidium staining. Fluorescence was visible for all labeling ratios. An increase in the intensity of the fluorescence from the lowest to highest labeling reagent to DNA ratios was also observed. The absolute extent of label incorporation was determined by measuring the absorbency of the purified samples at 576 nm ($\lambda_{max}$ for 5-(and-6)-carboxy-X-rhodamine, Molecular Probes Inc.). The absorption intensity at 576 nm was divided by the absorption intensity at 260 nm to correct for slight variations in the absolute amount of DNA present. Incorporation of labeling reagent is dependent on the amount of labeling reagent used, and is nearly linear before falling off at the higher ratios.

Example 9

Labeling Reagents can be covalently attached to DNA for use in DNA localization following cellular delivery.
(1) Materials
  1. pDNA (pCIluc) labeled with reagent 5 at two concentrations
  2. TransIT LT-1 transfection reagent (Mirus Corporation, Madison, Wis.)
  3. Cells (NIH 3T3 immortalized mouse fibroblast, ATTC, Rockville, Md.)
  4. fluorescence microscope (Leitz Orthoplan, Leitz Corporation, Germany)
(2) Procedure: Transfections were performed according to manufacturers recommendations. 2 µg DNA were transfected per 35 mm well. Cells were fixed and analyzed by fluorescence microscopy after 1 hour incubation.
(3) Results: Labeled DNA was observed in a punctate, perinuclear pattern. Strong fluorescent signal with low background was observed at both concentrations. No fluorescence was observed in cells transfected with unlabeled DNA.

Example 10

Figure 4:
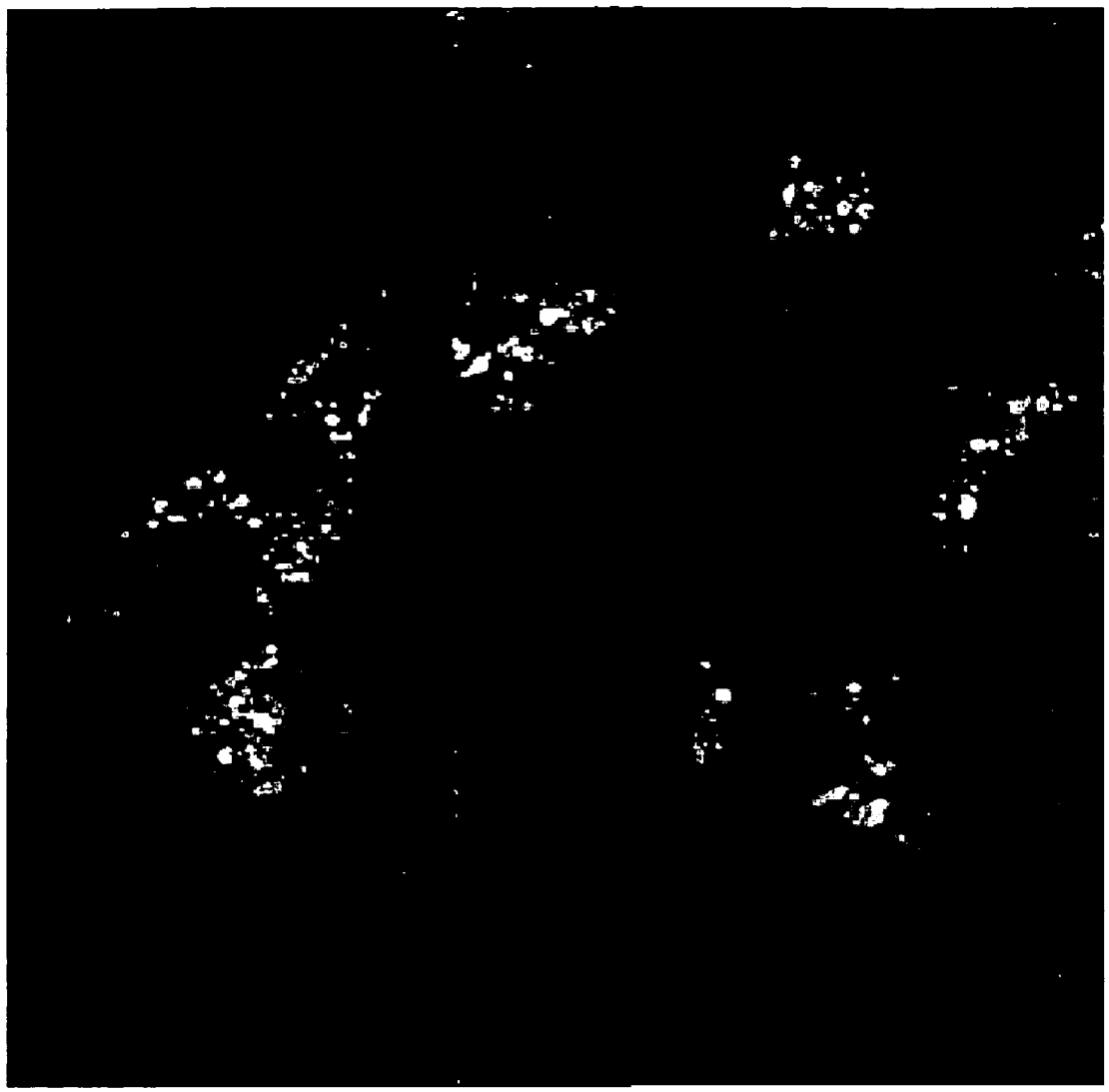
FIG. 4. SiRNA covalently labeled using the labeling reagent LABEL-IT®-Cyanine3 allows the visual tracking of siRNA delivered to a cell. Labeled siRNA was delivered to CHO cells with TRANSIT TKO®. Cyanine3-labeled siRNA is shown in white. Cells were visualized by reflected light and are shown in grey.

Labeling reagents can be covalently attached to small double strand RNA for use in siRNA localization following cellular delivery. SiRNA oligomers with overhanging 3' deoxynucleotides were prepared and purified by PAGE (Dharmacon, LaFayette, Colo.). The luciferase sense oligonucleotide had the sequence: 5'-rCrUrUrArCrGrCrUrGrAr-GrUrArCrU-rUrCrGrATT-3' (SEQ ID 1), corresponding to positions 155-173 of the reading frame. The luciferase antisense oligonucleotide had the sequence: 5'-rUrCr-GrArArGrUrArCrUrCrArG-rCrGrUrArArGTT-3' (SEQ ID 2) corresponding to positions 173-155 of the reading frame in the antisense direction. The letter "r" preceding a nucleotide indicates that the nucleotide is a ribonucleotide. The oligonucleotides were annealed in 100 mM NaCl/50 mM Tris-HCl, pH 8.0 buffer by heating to 94° C. for 2 min, cooling to 90° C. for 1 min, then cooling to 20° C. at a rate of 1° C. per minute. The annealed oligonucleotides are referred to as siRNA-GL3. The siRNAs were stored at −20° C. prior to use. 10 µg siRNAs was labeled by incubation with LABEL-IT®-Cyanine3 in 75 µl 20 mM MOPS pH 7.5 at 37° C. for 1 h. Labeled siRNA-GL3 was transfected into CHO, HeLa or 3T3 cells using TRANSIT-TKO® according to the manufacturer's recommendations. 24 h after transfection, cells were fixed for fluorescence microscopy. Fluorescence was detected using a Zeiss LSM 510 confocal microscope. Strong fluorescent signal with low background was observed (FIG. 4). Labeled siRNA was observed in a punctate pattern accumulating in the perinuclear region; a localization consistent with endocytic internalization of the siRNA. Cells are visible as reflected light at a different wavelength. No fluorescence was observed in cells transfected with unlabeled siRNA.

Example 11

Figure 5:
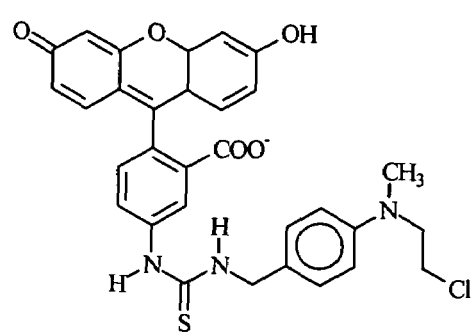
FIG. 5A-5F. The diagram in (A) illustrates the structure of an ineffective labeling reagent bearing a net charge of −1 at pH 7. (B) illustrates the reaction intermediate for (A) showing the positive charge gained. The diagram in (C) illustrates an effective labeling reagent bearing a net neutral charge. (D) illustrates the reaction intermediate for (C) showing the positive charge gained on the aziridine, bringing the net charge of the labeling reagent reactive species to +1. The diagram in (E) illustrates an ineffective labeling reagent bearing a net neutral charge. (F) illustrates the reaction intermediate for (E) showing no positive charge gained, leaving the net charge of the labeling reagent reactive species at neutral.
Figure 5:
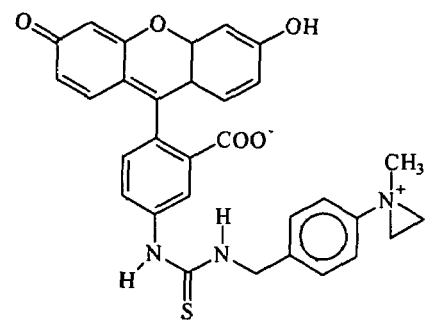
Figure 5:
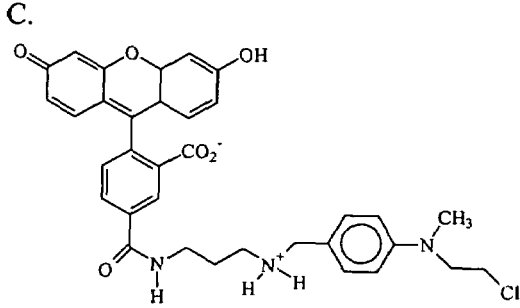
Figure 5:
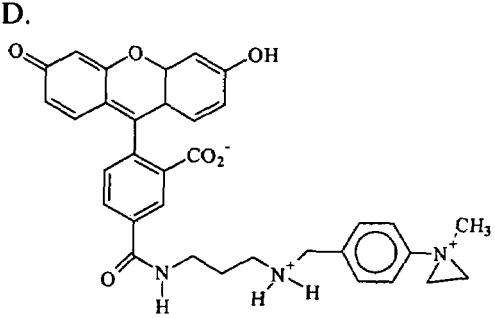
Figure 5:
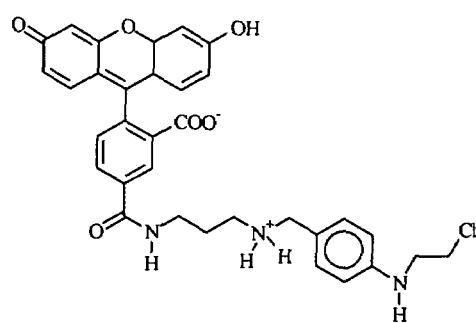
Figure 5:
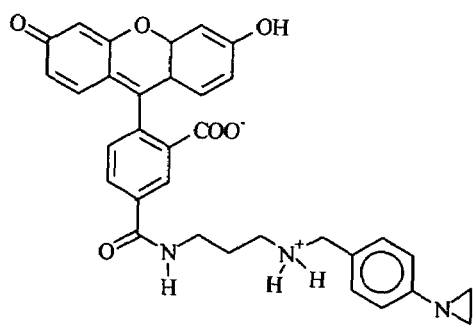

The labeling reagent must have affinity for nucleic acid when the labeling reaction occurs. The aromatic nitrogen mustard fluorescein reagent shown if FIG. 5A has a net charge of −1. During the alkylation reaction, a positively charged aziridine forms bringing the net charge of the labeling reagent intermediate to zero FIG. 5B. The FIG. 5A reagent was found to be unable to label nucleic acids. The reactive species does not have a charge greater than zero. In contrast, the aromatic nitrogen mustard fluorescein labeling reagent shown in FIG. 5C, has a net charge of zero. During the alkylation reaction a positively charged aziridine forms bringing the net charge this labeling reagent intermediate to +1, FIG. 5D. The FIG. 5C labeling reagent was found to efficiently label nucleic acids. The reagent shown in FIG. 5E has a neutral charge, but the nitrogen mustard for this reagent does not form a positively charged intermediate, FIG. 5F. This reagent is not predicted to efficiently label nucleic acid.

Example 12

Figure 6:
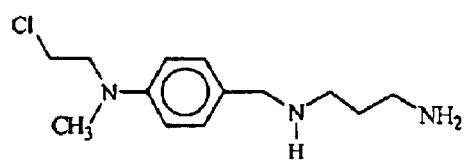
FIG. 6A-6E. Illustrations of labeling reagents having a net neutral charge. (A) LABEL-IT®-amine II was used in the synthesis of the shown neutral LABEL-IT® compounds. (B) neutral LABEL-IT®-Cyanine3. (C) neutral LABEL-IT®-Cyanine5. (D) neutral LABEL-IT®-PEG-Cyanine5. (E) neutral LABEL-IT®-ALEXA™488.
Figure 6:
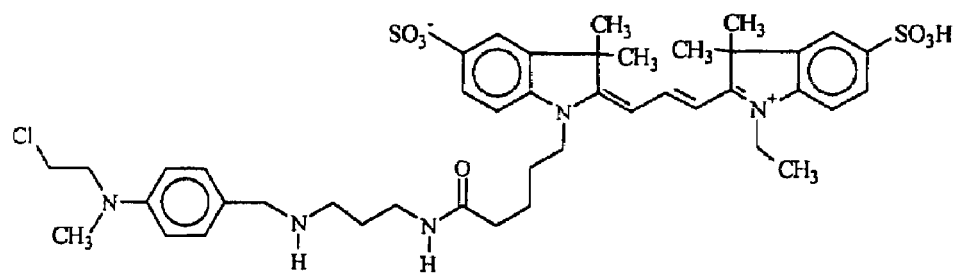
Figure 6:
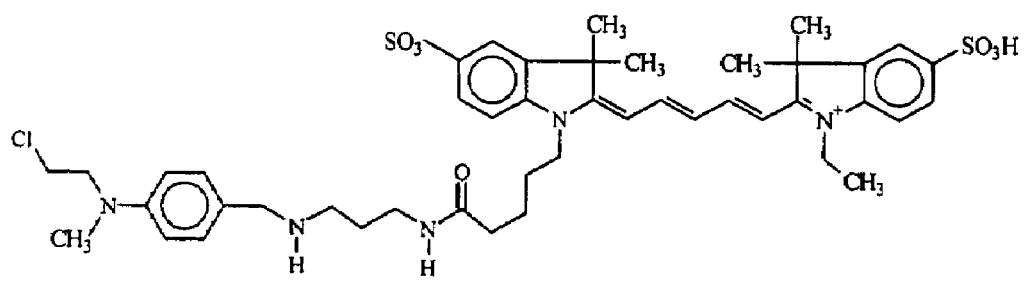
Figure 6:
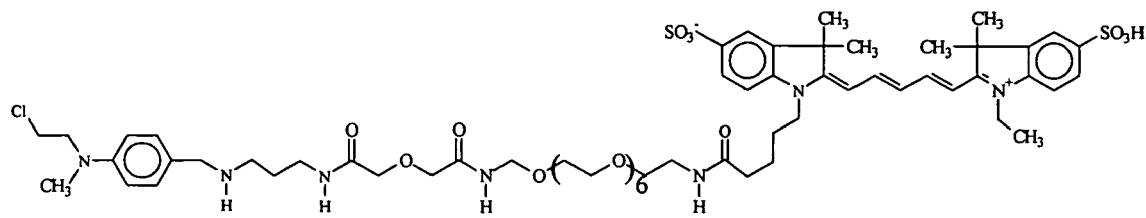
Figure 6:
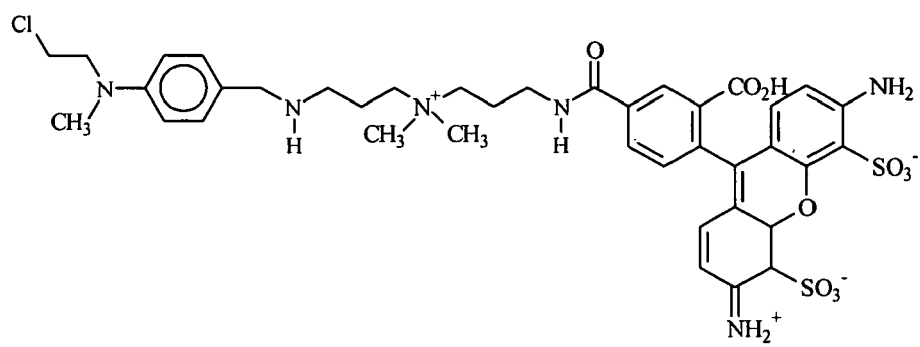

Use of labeling reagents for detection of nucleic acid in microarray applications. As described above, for labeling reagents containing tertiary amine nitrogen mustard alkylation groups, net neutral labeling reagents can be made that are effective in attaching a label to nucleic acid. Examples of such reagents are shown in FIG. 6. These net neutral labeling reagents were used in the preparation of fluorescent RNA and DNA probes for microarray/gene chip applications. RNA was obtained from total human reference RNA (Stratagene cat # 740000), or human liver or brain polyA RNA (Ambion cat # 7961 or 7660). First strand cDNA was obtained by reverse transcription of RNA. These nucleic acids were labeled with the indicated labeling reagents and hybridized to arrays of DNA fragments printed on coated glass slides.

cDNA: RNA was reverse transcribed to generate first-strand cDNA using Superscip™ II Rnase H⁻ Reverse Transcriptase (Invitrogen, cat # 18064-014) with an Oligo(dT) 12-18 primer (Invitrogen, cat # N420-01) according to manufacturer's recommendations. RNaseOUT Recombinant Ribonuclease Inhibitor (Invitrogen, cat# 10777-019) was included in the reaction to inhibit RNA degradation during synthesis. After cDNA synthesis, RNA was removed by incubation in 1 M NaOH/0.5 M EDTA at 65° C. for 30 minutes. cDNA was purified using the Qiagen QIAquick PCR Purification kit (cat # 28106) and eluted in 1 mM Tris (pH 8.0).

Fluorescent labeling of nucleic acid probes: The indicated labeling reagent was used at 0.5-3 µg labeling reagent per µg nucleic acid. Labeling reagent was incubated with nucleic acid for 1 h at 37° C. in 1.0 mM MOPS (pH 7.5) or 1 mM Tris (pH 8.0). Labeling reagent, in DMSO or methanol, was added to the nucleic acid such that the volume of labeling reagent was not more than 20% of the total reaction volume. Labeled probe was denatured by incubation in 0.1 volume 3 N NaOH for 5 min at RT and then neutralized by addition of 0.1 volume 1 M Tris pH 7.8, 3 N HCl and incubation at 0° C. for at least 5 min. Labeled nucleic acid probe was then purified by ethanol precipitation. For calculating labeling density, nucleic acids were resuspended in 1.0 mM MOPS (pH 7.5) or 1 mM Tris (pH 8.0), analyzed by spectrophotometry, and then lyophilized prior to hybridization.

Microarray Slides: Arrays were printed with a Genetix QArrayLite microarraying instrument according to the manufacturer's recommendations onto Aldehyde Slides (cat # K2630) or Amine Slides (cat # K2620) from Genetix (Hampshire, UK) or onto Slide Glass (cat # TX704) from TaKaRa (Shiga, Japan). Duplicate 12×12 arrays were printed on each slide using source DNA from a collection of 82 different human housekeeping genes (I.M.A.G.E. clones, Research Genetics HTVV Housekeeping Genes-002 R2 Jul. 18, 2001), positive PCR generated DNA controls, or negative controls (buffer, plasmid DNA, PCR products or salmon sperm DNA, Ambion cat # 9680). DNAs used for printing were stored at 0.1-0.2 µg/µl in 3×SSC in 384-well plates. Some genes were printed onto multiple locations in each array. Slide printing and processing were performed according to manufacturer's protocol. Pre-printed arrays were purchased from TaKaRa (Takara Intelligene TestARRAY version 3.0 (cat # X000).

Microarray Hybridization: Probes were hybridized to the above indicated slides as follows: 0.1-3.0 µg labeled nucleic acid probe, corresponding to 20-140 pmol dye, was resuspended in 10-30 µl hybridization buffer (50% formamide, 5×SSC, 0.1% SDS) containing hybridization blockers, 0-20 µg polyA RNA and 0-20 µg human cot-1 (Invitrogen, cat # 15279-011). DNA probes were denatured by incubation at 95° C. for 5 min. RNA probes were incubated at 65° C. for 5 min. Probes were then centrifuged at 16,000×g for 1 min, added to coverslips (Electron Microscopy Sciences cat #70329-22) and placed onto a printed microarray slides. Slides were incubated in Coming Hybridization Chambers (cat # 2551) overnight at 45° C. by submersion in a water bath. Slides were then washed 2×5 min in 1×SSC/0.2% SDS at 45° C., 1×5 min in 0.1×SSC/0.1% SDS at 45° C., and 1×5 min in 0.1×SSC at RT. Slides were then rinsed 3-5 times in $dH_2O$ and blown dry using compressed air.

Signal Detection: Slides were scanned with an Axon GenePix 4000B microarray scanner according to manufacturer's recommendations and analyzed using Axon GenPix Pro 4.0 software.

A. Probes labeled with charge neutral labeling reagents provide low non-specific binding in microarray applications. The following probes were made for use in hybridization to printed microarrays.

A and B: Human reference cDNA was labeled with LABEL-IT®-Cyanine3 labeling reagent (FIG. 3Aiii). Labeling density was calculated to be ~0.088 pmol Cyanine3 per ng cDNA. The array was probed with either (A) 340 ng labeled cDNA/30 pmol Cyanine3; or (B) 680 ng labeled cDNA/60.pmol Cyanine3.

C and D: Human reference cDNA was labeled with neutral LABEL-IT®-Cyanine3 labeling reagent (FIG. 6B). Labeling density was calculated to be ~0.051 pmol Cyanine3 per ng cDNA. The array was probed with either (C) 590 ng labeled cDNA/30 pmol Cyanine3; or (D) 1.2 µg labeled cDNA/60 pmol Cyanine3.

E and F: Human reference cDNA was labeled with primary amine LABEL-IT®-Cyanine3 labeling reagent. Labeling density was calculated to be 0.056 pmol Cyanine3 per ng cDNA. The array was probed with either (E) 540 ng labeled cDNA/30 pmol Cyanine3; or (F) 1.1 µg labeled cDNA/60 pmol Cyanine3.

Arrays and probes were prepared as described above. Source DNA included I.M.A.G.E. clone, β-actin and GAPDH DNA as well as negative control samples. Hybridized arrays were scanned and analyzed for fluorescence intensity using the Axon Genepix 4000B laser scanner and Genepix Pro 4.0 Array Acquisition and Analysis Software.

Figure 7:
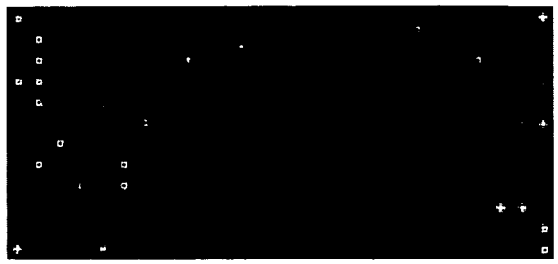
FIG. 7A-7F. Images of microarrays probed with Cyanine3-labeled human reference cDNA. Probes were labeled with: (A, B) LABEL-IT®-Cyanine3, (C, D) neutral LABEL-IT®-Cyanine3, or (E, F) amine LABEL-IT®-Cyanine3. Arrays were probed with either 30 pmol Cyanine3 (A, C, E) or 60 pmol Cyanine3 (B, D, F).
Figure 7:
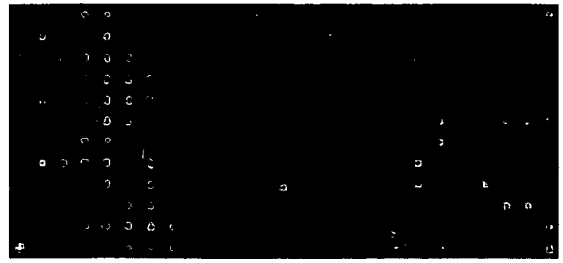
Figure 7:
Figure 7:
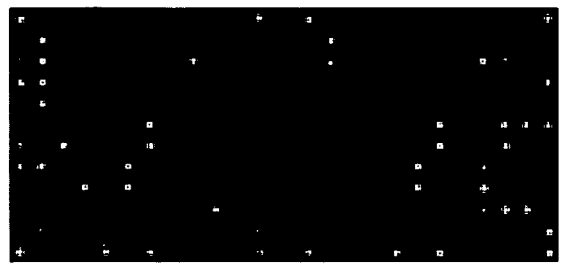
Figure 7:
Figure 7:
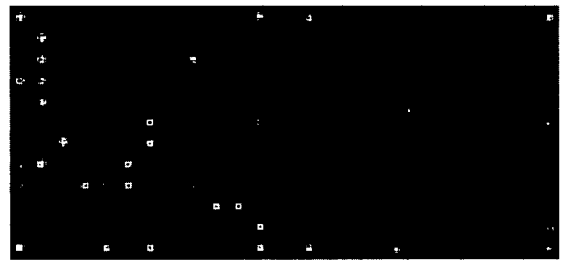

As shown the FIG. 7, the neutral labeling reagent (C and D) exhibits very little non-specific binding to the array slide. Conversely, positively charged labeling reagents (A, B, E, F) exhibited high non-specific binding. Specific fluorescent signal and background fluorescent signal, shown in Table 1, were determined by the Genepix Pro 4.0 Array Acquisition and Analysis Software Array Quality Control feature. The neutral LABEL-IT® labeling reagents reduced average background 2.4 to 5.6 fold and increased signal to background signals relative to the positively charged labeling reagents. For positively charged labeling reagents, average signal to background ratios were near 1. The neutral labeling reagent gave a much better signal to background ratio of 2.3-3.8 for whole array averages and a ratio of up to 41 for the maximum specific signal. Thus, the neutral LABEL-IT® labeling reagent is an effective reagent for covalently attaching a label to a nucleic acid in generating probes for use in microarray applications.

TABLE 1

Comparison of charge neutral vs. cationic labeling reagents in microarray hybridization.

| Labeling Reagent | Fluorescence signal | | | | |
| --- | --- | --- | --- | --- | --- |
| | Specific | Background | Ratio | Max. | Min. |
| LABEL-IT ®-Cyanine3 | | | | | |
| A. 30 pmol | 3371 | 3529 | 0.96 | 35160 | 714 |
| B. 60 pmol | 7541 | 8385 | 0.90 | 56659 | 1176 |
| neutral LABEL-IT ®-Cyanine3 | | | | | |
| C. 30 pmol | 3449 | 1480 | 2.3 | 39232 | 622 |
| D. 60 pmol | 5648 | 1493 | 3.8 | 61376 | 717 |
| primary amine LABEL-IT ®-Cyanine3 | | | | | |
| E. 30 pmol | 3476 | 2579 | 1.3 | 29174 | 1054 |
| F. 60 pmol | 6229 | 5102 | 1.2 | 65268 | 1530 |

Figure 8:
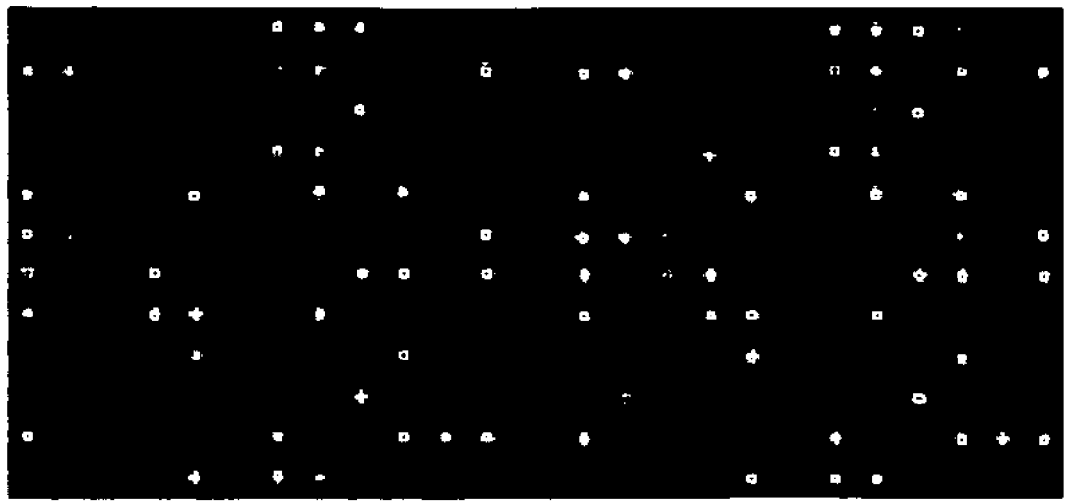
FIG. 8A-8B. Images of microarrays probed with: (A) human brain polyA RNA labeled with neutral LABEL-IT®-Cyanine3, (B) human liver polyA RNA labeled with neutral-LABEL-IT®-PEG-Cyanine5.
Figure 8:
Figure 9A:
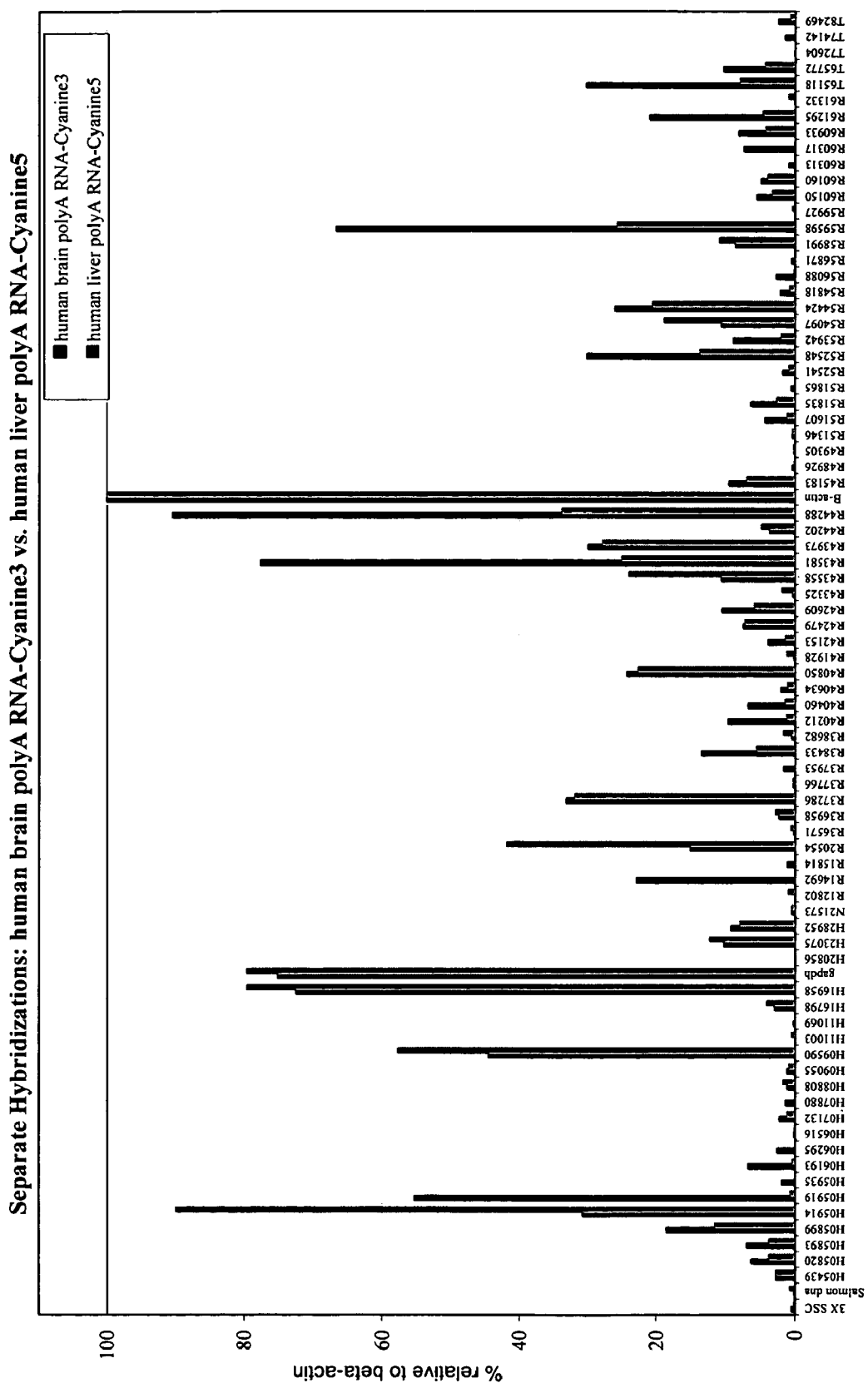
FIG. 9A-9B. Graphical representations of relative gene expression determined by microarray analysis using tissue specific RNA probes labeled with either neutral-LABEL-IT®-Cyanine3 or neutral-LABEL-IT®-PEG-Cyanine5 in either (A) single or (B) dual hybridizations. Gene expression is normalized to β-actin, which is set at 100%.
Figure 9B:
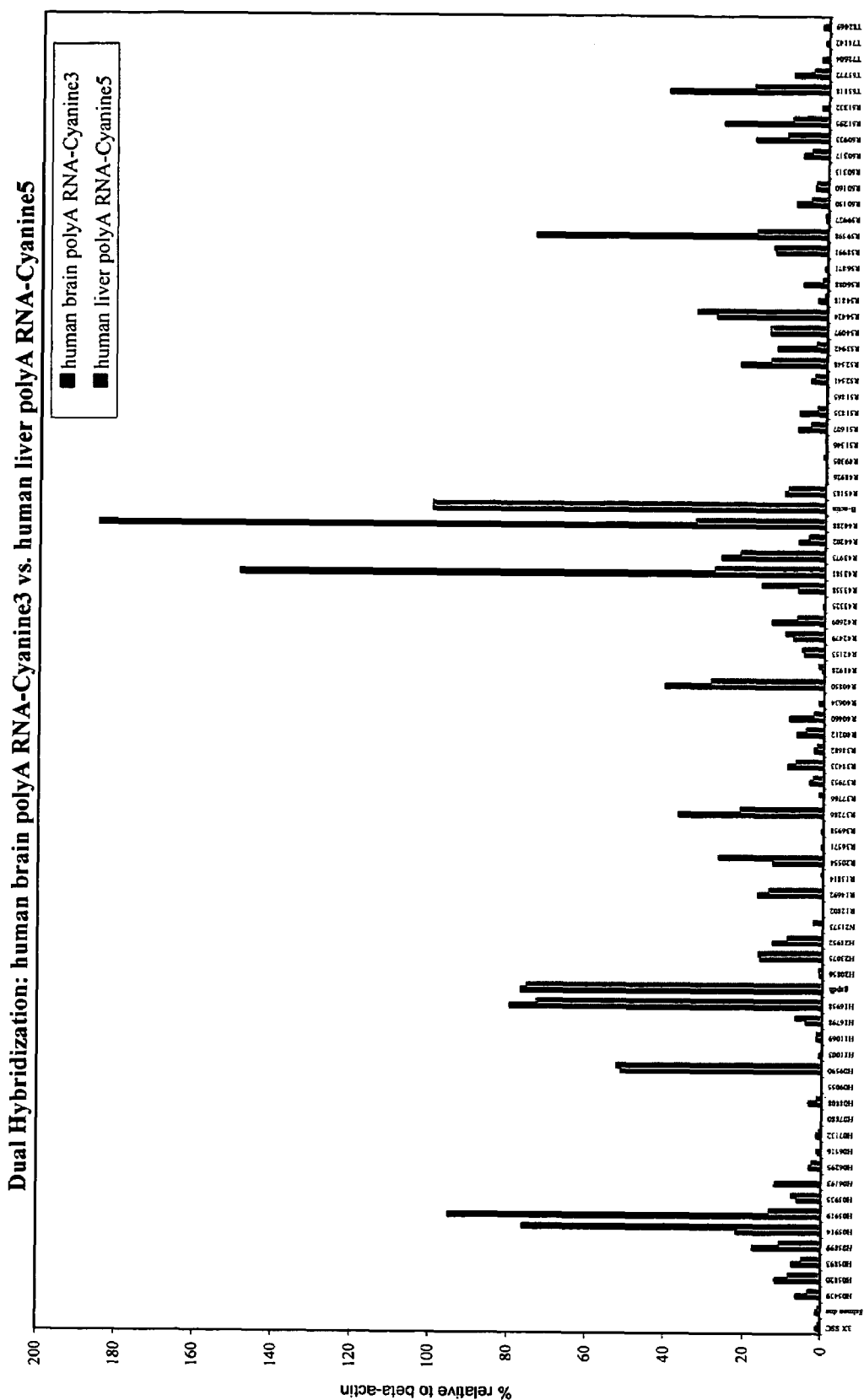

B. Probes labeled using the described neutral labeling reagents are useful in analyzing gene expression in microarray analyses. Human brain polyA RNA was labeled with neutral LABEL-IT®-Cyanine3 (FIG. 6B) to a density of 0.104 pmol Cyanine3 per ng RNA. Human liver polyA RNA was labeled with neutral LABEL-IT®-PEG-Cyanine5 (FIG. 6D) to a density of 0.043 pmol Cyanine5 per ng RNA. 250 ng human brain polyA RNA-Cyanine3 probe (FIGS. 8A and 9A), 1.0 µg human liver polyA RNA-Cyanine5 probe (FIGS. 8B and 9A), or 150 ng brain polyA RNA-Cyanine3+1.0 µg liver polyA RNA-Cyanine5 probe (FIG. 9B) were then hybridized to amine coated slide arrays. Each array includes common high expression housekeeping genes such β-actin and GAPDH (from I.M.A.G.E. clones) and a GAPDH PCR product as well as the negative control samples 3×SSC (no DNA present), sheared salmon sperm DNA and non-human luciferase gene PCR product. Some samples were spotted onto multiple locations in the array. Clones and array positions are given in Table 2. Hybridized arrays were scanned and analyzed for fluorescence intensity using the Axon Genepix 4000B laser scanner and Genepix Pro 4.0 Array Acquisition and Analysis Software. Signal intensity for each spot was normalized to fluorescence emission values for the P-actin clones, which were set at 100%. FIGS. 8 and 9 and Table 2 show the expression levels observed for different genes and for different probes for both single and dual probe hybridizations.

TABLE 2

Microarray analysis of gene expression using liver or brain polyA RNA probes fluorescently labeled with Cyanine3 and Cyanine5 labeling reagents in single probe and dual probe hybridizations.

| | | gene expression[c] | | | |
|---|---|---|---|---|---|
| | | single probe | | dual probe | |
| gene[a] | array location[b] | brain-Cyanine3 | liver-Cyanine5 | brain-Cyanine3 | liver-Cyanine5 |
| 3X SSC | B4, B9, D2, D9, E6, H6, I2, I9, K4, K9 | 0.49 | 0.20 | 1.08 | 0.53 |
| salmon DNA | A2, A11, E7, G6, G8, L2, L11 | 0.10 | 0.68 | 1.19 | 0.70 |
| H05439 | K3 | 2.72 | 2.74 | 6.49 | 3.27 |
| H05820 | K6 | 6.27 | 3.71 | 11.8 | 8.29 |
| H05893 | E4, K2 | 6.94 | 3.71 | 7.35 | 4.91 |
| H05899 | D7 | 18.4 | 11.5 | 17.5 | 10.9 |
| H05914 | A9 | 30.8 | 90.0 | 21.6 | 76.3 |
| H05919 | J9 | 55.2 | 0.59 | 95.2 | 13.3 |
| H05935 | L10 | 1.88 | −0.68 | 6.26 | 7.59 |
| H06193 | J11 | 6.69 | 0.39 | 12.0 | −0.12 |
| H06295 | C4, H2 | 2.49 | −0.20 | 3.10 | 2.57 |
| H06516 | G11 | 0.14 | 0.10 | 1.04 | −1.40 |
| H07132 | D1, F4 | 2.19 | 1.08 | 1.22 | 0.58 |
| H07880 | E3 | 1.31 | −2.20 | −0.44 | −0.82 |
| H08808 | I3 | 1.01 | 1.66 | 3.30 | 1.23 |
| H09055 | A3 | 1.03 | 0.78 | −1.43 | 0.00 |
| H09590 | H1, H4 | 44.4 | 57.7 | 51.0 | 52.0 |
| H11003 | L4 | −0.15 | 0.49 | 0.74 | 0.23 |
| H11069 | I1, I4, J4 | 0.21 | −0.20 | 1.45 | 1.40 |
| H16798 | H3 | 2.88 | 4.06 | 4.13 | 6.95 |
| H16958 | G4, E1 | 72.4 | 79.6 | 79.6 | 72.6 |
| GAPDH | A7, B1, B12, E5, E8, F1, F12, G1, G12, H5, H8, K1, K12, L7 | 75.1 | 79.6 | 77.0 | 75.5 |
| H20856 | L3 | −0.16 | −0.59 | 0.74 | 0.93 |
| H23075 | F3 | 10.1 | 12.2 | 15.9 | 16.6 |
| H28952 | G3 | 9.15 | 7.92 | 12.71 | 9.00 |
| N21573 | D3 | 0.48 | 0.54 | −0.80 | 2.45 |
| R12802 | C2, J5 | −0.03 | 0.88 | −0.99 | −0.23 |
| R14692 | B8 | 22.8 | 0.00 | 16.8 | 13.8 |
| R15814 | B3 | 1.04 | −0.20 | 0.04 | 0.47 |
| R20554 | D8 | 15.0 | 41.8 | 12.9 | 26.9 |
| R36571 | E12 | 0.19 | 0.59 | 0.47 | −1.40 |
| R36958 | C6 | 2.25 | 2.69 | 0.44 | 0.06 |
| R37286 | E10 | 33.1 | 31.9 | 37.0 | 21.3 |
| R37766 | F9 | 0.25 | 0.29 | 0.18 | 1.29 |
| R37953 | L6 | 1.59 | 0.00 | 3.58 | 2.69 |
| R38433 | B7 | 13.4 | 5.47 | 9.24 | 7.13 |
| R38682 | I12 | 0.46 | 1.66 | 2.49 | 1.64 |
| R40212 | A10 | 9.61 | 1.17 | 7.08 | 4.38 |
| R40460 | G5 | 6.67 | 1.42 | 8.85 | 2.63 |
| R40634 | E2, K5 | 1.99 | 1.08 | 1.32 | −0.29 |
| R40850 | L8 | 24.3 | 22.6 | 40.7 | 29.0 |
| R41928 | H11 | 0.14 | 1.17 | 0.60 | 1.52 |
| R42153 | H9 | 3.83 | 1.37 | 5.12 | 5.61 |
| R42479 | C7 | 7.41 | 7.18 | 8.02 | 10.05 |
| R42609 | F10 | 10.4 | 5.82 | 13.5 | 7.01 |
| R43325 | D12 | 0.30 | 1.86 | 0.49 | −0.06 |
| R43558 | B5 | 10.5 | 23.9 | 6.78 | 16.2 |
| R43581 | K11 | 77.6 | 25.0 | 148.9 | 28.2 |
| R43973 | F2, L5 | 29.9 | 27.7 | 26.5 | 21.5 |
| R44202 | I8 | 3.61 | 4.79 | 6.73 | 4.15 |
| R44288 | K10 | 90.5 | 33.7 | 185 | 32.9 |
| β-actin | G9 | 100 | 100 | 100 | 100 |
| R45183 | C11 | 9.50 | 6.89 | 10.3 | 9.46 |
| R48926 | C5 | 0.44 | 0.10 | −1.12 | −0.23 |
| R49305 | A4, G2 | 0.14 | 0.24 | −0.39 | 0.70 |
| R51346 | D11 | 0.38 | 0.39 | −0.03 | 0.35 |
| R51607 | I7 | 4.32 | 1.17 | 7.18 | 3.86 |
| R51835 | B10, H12 | 6.32 | 2.57 | 6.79 | 2.28 |
| R51865 | D5 | 0.59 | −1.12 | −0.73 | −0.70 |
| R52541 | J8 | 1.78 | 0.88 | 4.01 | 2.92 |
| R52548 | A8 | 30.1 | 13.7 | 21.9 | 14.1 |
| R53942 | H10 | 8.87 | 2.05 | 12.80 | 2.69 |
| R54097 | D4, J2 | 10.5 | 18.8 | 14.4 | 14.5 |
| R54424 | B2, I5 | 26.0 | 20.4 | 28.1 | 33.1 |
| R54818 | E11 | 2.17 | 0.78 | 2.18 | 0.58 |
| R56088 | J7 | 2.63 | 0.20 | 6.08 | 1.11 |
| R56871 | I6 | 0.51 | −0.68 | 0.65 | −1.05 |
| R58991 | F5 | 8.56 | 10.9 | 13.2 | 13.7 |
| R59598 | C9 | 66.7 | 25.6 | 74.2 | 18.0 |
| R59927 | F11 | 0.03 | 0.39 | 0.45 | 0.64 |
| R60150 | J6 | 5.52 | 3.23 | 7.97 | 4.21 |
| R60160 | A5 | 4.87 | 3.91 | 3.17 | 2.80 |
| R60313 | A6, B11 | 0.81 | −1.03 | −0.88 | −1.64 |
| R60317 | D6 | 7.34 | −1.76 | 6.26 | 4.21 |
| R60933 | L9 | 8.10 | 4.20 | 18.6 | 10.3 |
| R61295 | I10 | 20.9 | 4.59 | 26.6 | 9.00 |
| R61332 | I11 | 0.04 | 0.83 | 1.61 | −0.12 |
| T65118 | K7 | 30.2 | 7.92 | 40.5 | 18.9 |
| T65772 | C8 | 10.3 | 4.30 | 8.85 | 3.68 |
| T72604 | K8 | 0.03 | −0.05 | 1.74 | −0.12 |
| T74142 | D10 | 1.48 | −0.29 | 0.64 | 0.06 |
| T82469 | E9 | 2.46 | 0.68 | 1.55 | 0.23 |
| R44334 | G10 | nq[d] | | | |
| R49530 | B6 | nq | | | |
| luciferase | A1, A12, C3, C10, F7, G7, J3, J10, L1, L12 | nq | | | |
| plasmid DNA | C1, C12, F6, F8, H7, J1, J12 | nq | | | |

[a]gene listed by either gene name, DNA description, or Genbank accession number
[b]rows are labeled A through L, columns are labeled 1–12 (note: the array is duplicated on each slide)
[c]expression given as a percent of β-actin expression, which was arbitrarily set at 100%
[d]data not queried Conclusions: The data in FIGS. 8 and 9 and in Table 2 show that RNA probes labeled with both neutral LABEL-IT®-Cyanine3 (FIG. 8A) and neutral LABEL-IT®-PEG-Cyanine5 (FIG. 8B) hybridized to DNA on the array with high specificity and with low background binding of probe to the array slide. Also, the labeling reagent did not cause binding to either buffer samples or to negative control DNA samples. Average specific fluorescence intensities for selected genes and controls are shown in Table 3. Specific β-actin signal was 4.8-30.3-fold higher than background using probes labeled with the neutral labeling reagents.

TABLE 3

Microarray signal to background ratios for probes fluorescently labeled with neutral LABEL-IT ®-Cyanine3 and neutral LABEL ®-IT-Cyanine5.

| Probe | Cyanine3 signal intensity | | | Cyanine5 signal intensity | | |
|---|---|---|---|---|---|---|
| | β-actin | background | ratio | β-actin | background | ratio |
| brain polyA RNA-Cyanine3 | 11842 | 391 | 30.3 | | | |
| liver polyA RNA-Cyanine5 | | | | 2518 | 471 | 5.3 |
| brain polyA RNA-Cyanine3 + liver polyA RNA-Cyanine5 | 8362 | 671 | 12.5 | 2165 | 453 | 4.8 |

The data further show that RNA probes labeled with both neutral LABEL-IT®-Cyanine3 and neutral LABEL-IT®-PEG-Cyanine5 can be used in array technology to analyze gene expression. Differences in gene expression within a tissue as well as tissue specific similarities and differences in gene expression were readily detected and quantitated using probes labeled with both labeling reagents. For example, Genes H05919, R43581 and R44288 showed much greater expression in brain than in liver, whereas H05914 and R20554 showed much higher expression in liver and H09590 and R43973 showed similar gene expression in both tissues. Genes expected to be expressed at similar levels in both tissues, such as GAPDH, gave similar relative expression values. Statistically identical signals were obtained for GAPDH expression whether the array was spotted with an I.M.A.G.E. clone or with a PCR product.

Finally, measurement of gene expression was independent of the presence of one or two probes during the hybridization. This comparison shows that reliable data can be obtained in both single and dual probe hybridizations using probes labeled with neutral LABEL-IT®-Cyanine3 and neutral LABEL-IT®-PEG-Cyanine5.

C. The described neutral labeling reagents effectively label total RNA, first strand synthesis cDNA and double stranded DNA for use in microarray applications.

A) Total human reference RNA, 0.5 µg, was labeled with neutral LABEL-IT®-Cyanine3. Labeling density was calculated to be ~0.124 pmol Cyanine3 per ng RNA.

B) First-strand human reference cDNA reverse transcribed from total human reference RNA, 1.0 µg, was labeled with neutral LABEL-IT®-PEG-Cyanine5. Labeling density was calculated to be ~0.038 pmol Cyanine5 per ng cDNA.

C) Luciferase 1.6 kb PCR product, 1.0 µg, was labeled with neutral LABEL-IT®-PEG-Cyanine5. Labeling density was calculated to be ~0.017 pmol Cyanine5 per ng DNA. Labeled probes were then hybridized to separate arrays.

Arrays for (A) and (B) were printed using I.M.A.G.E. clones and PCR products and included common high expression housekeeping genes, such β-actin and GAPDH. These arrays also included the negative control samples: 3×SSC (no DNA present), sheared salmon sperm DNA and non-human luciferase gene PCR product. Some, samples were spotted onto multiple locations in the array. The array for (C) was printed using varying amounts of a luciferase 1.6 kb PCR product, β-actin or GAPDH source DNA. β-actin and GAPHD served as negative control DNAs this array. This array also contained 3×SSC negative control spots. Genes, source DNA concentration and replicates for the array in (C) are shown in Table 5.

Figure 10:
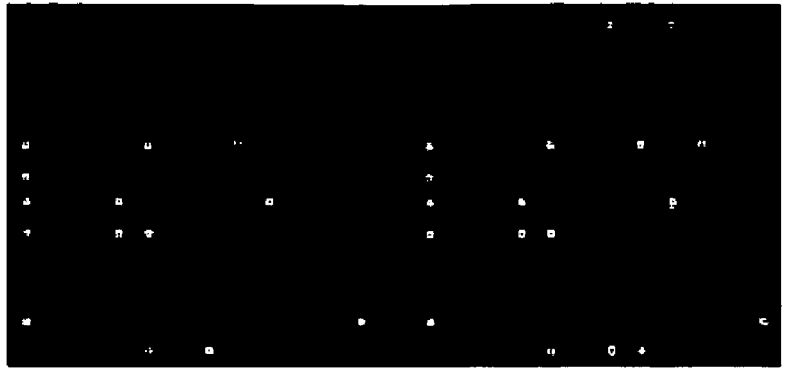
FIG. 10A-10C. Images of microarrays probed with: (A) Total human reference RNA labeled with neutral LABEL-IT®-Cyanine3, (B) first-strand human reference cDNA reverse transcribed from total human reference RNA and labeled with neutral LABEL-IT®-PEG-Cyanine5, and (C) Luciferase 1.6 kb PCR product labeled with neutral LABEL-IT®-PEG-Cyanine5.
Figure 10:
Figure 10:

Hybridized arrays were scanned and analyzed for fluorescence intensity using the Axon Genepix 4000B laser scanner and Genepix Pro 4.0 Array Acquisition and Analysis Software. The data are shown in FIG. 10 and in Tables 4 and 5. For arrays (A) and (B), FIGS. 10A and 10B respectively, signal intensity for each spot was normalized to the average fluorescence emission value for the β-actin clones, which was set at 100%.

Conclusions: These data demonstrate that the neutral LABEL-IT®-Cyanine3 and neutral LABEL-IT®-PEG-Cyanine5 labeling reagents can be used to label RNA (FIG. 10A), first-strand cDNA (FIG. 10B) and double stranded DNA (FIG. 10C). The resultant probes are then effective in microarray applications. The data in Table 5 further show that the neutral LABEL-IT®-PEG-Cyanine5 labeled probes provide detectable signal when 0.00125 µg/µl DNA and even as little as 0.00625 µg/µl DNA is printed on the array.

Example 13

Figure 11:
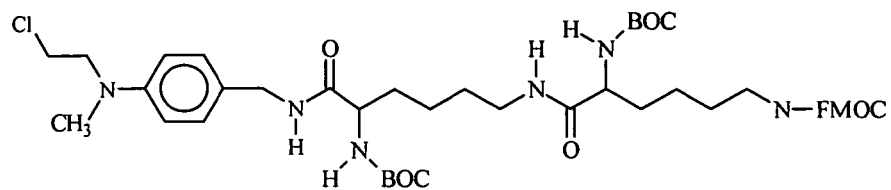
FIG. 11. Illustrations of labeling reagents having a reversible charge. (A) charge reversible LABEL-IT® which was an intermediate in the synthesis of: (B) charge reversible LABEL-IT®-Cyanine3, and (C) charge reversible LABEL-IT®-CX-Rhodamine. (D) is an illustration of charge reversible LABEL-IT®-CX-Rhodamine after covalent attachment of the labeling reagent to nucleic acid (quanine nucleotide) and reversal the positive charges on the labeling reagent by reaction with succinic anhydride.
Figure 11:
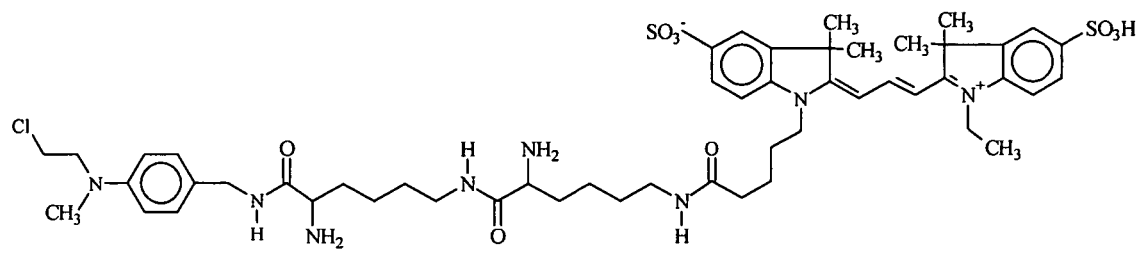
Figure 11:
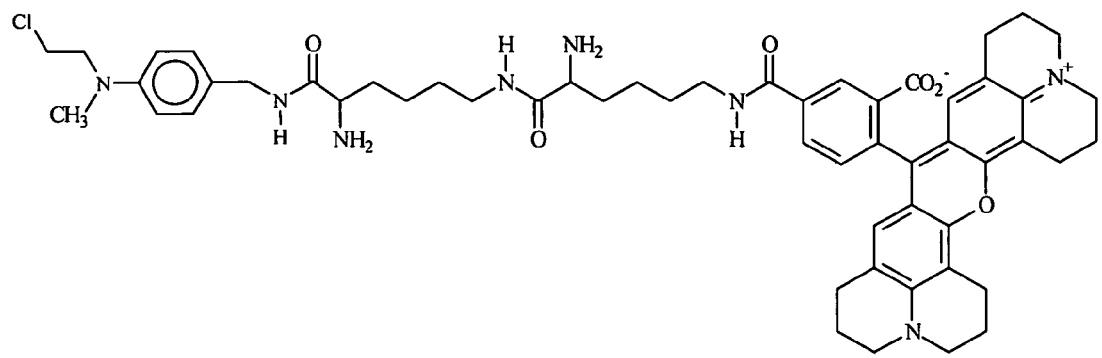
Figure 11:
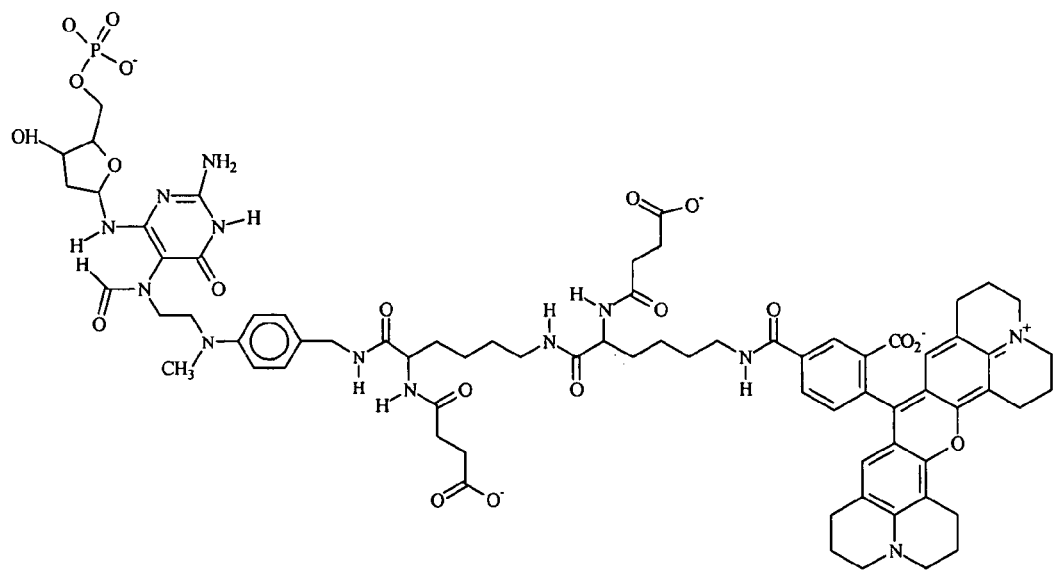

Charge reversible labeling reagents. We have developed labeling reagents designed to contain reversible charge. The reagents contain positive charge(s) which can be converted to negative charge(s) after the reagent has covalently attached to a target molecule. Examples of these reagents are shown in FIG. 11. FIG. 11A shows an illustration of the molecule to which a fluorescent compound is attached by replacement of the FMOC protecting group to form the labeling reagents illustrated in FIGS. 11B and 11C. FIG. 11D shows an illustration of the charge reversible labeling reagent shown in FIG. 11C after the compound has covalently attached to a guanine nucleotide and had the positively charged primary amines converted to carboxyls by reaction with succinic anhydride.

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

TABLE 4

Described charge neutral labeling reagents effectively label total RNA and first strand synthesis cDNA for use in microarray applications.

| Gene[a] | n | A) RNA-Cyanine3 | B) cDNA-Cyanine5 | Gene[a] | n | A) RNA-Cyanine3 | B) cDNA-Cyanine5 |
|---|---|---|---|---|---|---|---|
| 3X SSC | 28 | −1.07 | 0.43 | R41928 | 2 | 4.74 | −0.25 |
| salmon DNA | 14 | 10.3 | 0.19 | R42153 | 2 | 1.95 | 2.41 |
| H05439 | 2 | 1.56 | 2.66 | R42479 | 2 | −5.62 | 0.28 |
| H05820 | 2 | 6.56 | 11.2 | R42609 | 2 | 2.60 | 5.94 |
| H05893 | 4 | 0.88 | 19.3 | R43325 | 2 | −0.68 | −0.62 |
| H05899 | 2 | −0.57 | 28.1 | R43558 | 2 | −6.48 | 10.5 |
| H05914 | 2 | 26.6 | 43.3 | R43581 | 2 | 39.6 | 85.2 |
| H05919 | 2 | 5.05 | 9.80 | R43973 | 4 | 45.2 | 83.5 |
| H05935 | 2 | 12.0 | 2.41 | R44202 | 2 | 3.64 | 16.9 |
| H06193 | 2 | 7.39 | 0.09 | R44288 | 2 | 26.1 | 27.5 |
| H06295 | 4 | −2.97 | 2.91 | β-actin | 2 | 100 | 100 |
| H06516 | 2 | 3.07 | −0.15 | R45183 | 2 | 1.33 | 22.1 |
| H07132 | 4 | −5.20 | 0.62 | R48926 | 2 | −7.05 | −0.25 |
| H07880 | 2 | −5.41 | 1.36 | R49305 | 4 | −6.38 | −0.06 |
| H08808 | 2 | −0.68 | 2.41 | R51346 | 2 | −2.03 | −0.31 |
| H09055 | 2 | −8.48 | 6.56 | R51607 | 2 | 0.88 | 6.80 |
| H09590 | 4 | 71.4 | 98.6 | R51835 | 2 | 8.01 | 0.25 |
| H11003 | 2 | 6.43 | 2.1 | R51835 | 2 | −3.59 | 1.61 |
| H11069 | 2 | 0.47 | 2.63 | R51865 | 2 | −5.46 | −1.67 |
| H16798 | 2 | 2.97 | 20.8 | R52541 | 2 | 2.76 | 2.94 |
| H16958 | 4 | 73.8 | 80.1 | R52548 | 2 | −5.98 | 15.6 |
| GAPDH | 28 | 52.7 | 61.0 | R53942 | 2 | 3.33 | 8.81 |
| H20856 | 2 | 2.89 | 1.92 | R54097 | 4 | 0.65 | 16.9 |
| H23075 | 2 | −2.94 | 10.6 | R54424 | 4 | −2.78 | 9.59 |
| H28952 | 2 | −0.29 | 22.4 | R54818 | 2 | 0.62 | −0.15 |
| N21573 | 2 | −6.12 | 0.40 | R56088 | 2 | 1.80 | 1.30 |
| R12802 | 4 | −4.01 | 0.19 | R56871 | 2 | −1.20 | 1.33 |
| R14692 | 2 | −5.62 | 14.2 | R58991 | 2 | −0.47 | 8.04 |
| R15814 | 2 | −7.55 | −1.79 | R59598 | 2 | 13.2 | 40.8 |
| R20554 | 2 | 1.93 | 19.2 | R59927 | 2 | 1.25 | 0.00 |
| R36571 | 2 | 0.60 | 0.37 | R60150 | 2 | 6.25 | 13.0 |
| R36958 | 2 | −5.20 | 2.57 | R60160 | 2 | −7.23 | 7.85 |
| R37286 | 2 | 38.3 | 38.1 | R60313 | 2 | 0.31 | −1.98 |
| R37766 | 2 | −0.57 | −0.19 | R60313 | 2 | −7.21 | −0.06 |
| R37953 | 2 | 6.51 | 4.45 | R60317 | 2 | −4.06 | 7.2 |
| R38433 | 2 | −1.25 | 9.03 | R60933 | 2 | 14.4 | 24.9 |
| R38682 | 2 | 7.65 | 0.43 | R61295 | 2 | 13.8 | 47.0 |
| R40212 | 2 | −4.89 | 11.8 | R61332 | 2 | 5.41 | −0.06 |
| R40460 | 2 | −0.52 | 6.43 | T65118 | 2 | 6.82 | 18.4 |
| R40634 | 4 | −1.98 | 2.54 | T65772 | 2 | −2.81 | 21.1 |
| R40850 | 2 | 59.9 | 77.1 | T72604 | 2 | 5.10 | 0.22 |

[a]listed by description, gene name, or Genebank accession number

TABLE 5

Detection of varying levels of printed source DNA using neutral LABEL-IT ®-PEG-Cyanine5 labeled Luciferase dsDNA.

| gene | source DNA µg/µl | replicates | signal intensity |
|---|---|---|---|
| 3X SSC | 0.0 | 20 | 8 |
| luciferase | 0.000625 | 20 | 48 |
|  | 0.00125 | 16 | 354 |
|  | 0.0025 | 20 | 602 |
|  | 0.005 | 20 | 1308 |
|  | 0.01 | 18 | 2380 |
|  | 0.02 | 20 | 3729 |
|  | 0.05 | 16 | 5800 |
|  | 0.1 | 16 | 2248 |
|  | 0.2 | 20 | 1564 |
| β-actin | 0.00125 | 2 | 14 |
|  | 0.01 | 2 | −12 |
|  | 0.05 | 2 | 25 |
|  | 0.1 | 2 | 16 |
| GAPDH | 0.00125 | 2 | −4 |
|  | 0.05 | 2 | −18 |
|  | 0.1 | 2 | 58 |

REFERENCES

Adarichev V A, Vorobeva N V, Grafodatskii A S, Dymshits G M, Sablina O V Adarichev. "DNA Modification with 4-Aminohydroxybutylamine to Obtain Highly Sensitive Hybridization Probes. Location of Human Chorionic Somatomammotropin Gene." *Molecular Biology* 1995; Vol. 29; No. 3; Part 1; 307-311.

Belikova, A. M. et al., "Xylation of Nucleic Acids and Their Components: Alkylation of Nucleosides By 4-[N-(-Chloroethyl)-[Ethylamino]Benzaldehyde." Translated from *Khimiya Geterotsiklicheskikh Soedinenii* 1972; Vol. 1; 109-116.

Belikova A M, Zarytova V F, Grineva N I. "Synthesis of Ribonucleosides and Diribonucleoside Phosphates Containing 2-Chloroethylamine and Nitrogen Mustard Residues." *Tetrahedron Letters;* 1967; Vol. 37; 3557-3562.

Caspersson T, Zech L, Modest E J, Foley G E, Wagh U, Simonsson E Caspersson, T. "Chemical Differentiation with Fluorescent Alkylating Agents in Vicia Faba Metaphase Chromosomes." *Experimental Cell Research;* 1969; Vol. 58; 128-140.

Danko I, Williams P, Herweijer H, Zhang G, Latendresse J S, Bock I, Wolff J A. "High expression of naked plasmid DNA in muscles of young rodents." *Human Molecular Genetics* 1997; Vol. 6; No. 9; 1435-43.

Elbashir S M, Harborth J, Lendeckel W, Yalcin A, Weber K, Tuschl T. "Duplexes of 21-nucleotide RNAs mediate RNA interference in cultured mammalian cells." *Nature* 2001; Vol. 411; 494-498.

Elbashir S M, Lendeckel W, Tuschl T. "RNA interference is mediated by 21- and 22-nucleotide RNAs." *Genes and Development* 2001; Vol. 15; 188-200.

Frumgarts L A, Kipriyanov S M, Kalachikov S M, Dudareva N A, Dymshits G M, Karpova G G, Salganik R I. "Preparation of Fluorescently Labeled DNA and Its Use as a Probe in Molecular Hybridization." Translated from *Bioorganicheskaya Khimiya* 1986; Vol. 12; No. 11; 1508-1513.

Landegent, J. E. et al., "2-Acetylaminofluorene-modified Probes for the Indirect Hybridocytochemical Detection of Specific Nucleic Acid Sequences." *Experimental Cell Research* 1984; Vol. 153; 61-72.

Sharp P A. "RNA interference—2001." *Genes and Development* 2001 Vol. 15; 485-490.

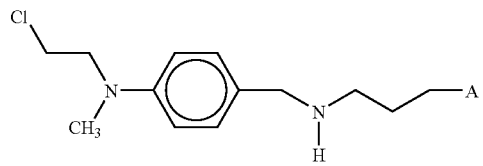

wherein A comprises a label and wherein the compound bears a net neutral charge and the aromatic nitrogen mustard becomes positively charged during the alkylation reaction.

2. The compound of claim 1 wherein the label is selected from the group consisting of fluorescence-emitting molecules, hapten-containing molecules, proteins, and radioactive chemicals.

3. The compound of claim 1 wherein the label is selected from the group consisting of functional groups.

4. The compound of claim 1 wherein the label is separated from the alkylating group by a linker.

5. The compound of claim 4 wherein the label has a net charge and the linker has a net charge opposite that of the label.

6. The compound of claim 1 wherein the nucleic acid consists of DNA.

7. The compound of claim 1 wherein the nucleic acid consists of RNA.

8. The compound of claim 7 wherein the nucleic acid consists of siRNA.

9. A labeling compound for covalently attaching a label to a nucleic acid in a single-pot reaction comprising: an aromatic mustard alkylating group, a label, and a spacer wherein the spacer contains at least one primary amine that can be reacted with a molecule to convert the primary amine to a negatively charged functional group after the labeling compound has been covalently attached the nucleic acid.

We claim:

1. A labeling compound for covalently attaching a label to a nucleic acid in a single-pot reaction comprising the structure:

10. The compound of claim 9 wherein the aromatic mustard consists of an aromatic tertiary mustard.

11. The compound of claim 10 wherein the aromatic tertiary mustard consists of an aromatic tertiary nitrogen mustard.

12. The compound of claim 11 wherein the label is selected from the group consisting of fluorescence-emitting molecules, hapten-containing molecules, proteins, and radioactive chemicals.

13. The compound of claim 11 wherein the label is selected from the group consisting of functional groups.

14. The compound of claim 11 wherein the function groups consists of a primary amine.

15. The compound of claim 11 wherein the nucleic acid consists of DNA.

16. The compound of claim 11 wherein the nucleic acid consists of RNA.

17. The compound of claim 16 wherein the nucleic acid consists of siRNA.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Photinus pyralis

<400> SEQUENCE: 1
cuuacgcuga guacuucgat t                                              21

<210> SEQ ID NO 2
<211> LENGTH: 21
<212> TYPE: DNA
<213> ORGANISM: Photinus pyralis

<400> SEQUENCE: 2
ucgaaguacu cagcguaagt t                                              21